US009355374B2

(12) United States Patent
Barnett et al.

(10) Patent No.: US 9,355,374 B2
(45) Date of Patent: May 31, 2016

(54) SYSTEMS AND METHODS FOR CREATING FINGERPRINTS OF ENCRYPTION DEVICES

(71) Applicant: Capital Payments, LLC, Atlanta, GA (US)

(72) Inventors: Timothy William Barnett, Roswell, GA (US); Alexander I. Kasatkin, Alpharetta, GA (US); Christopher Hozumi Miyata, Tulsa, OK (US)

(73) Assignee: Bluefin Payment Systems LLC, Sandy Springs, GA (US)

( * ) Notice: Subject to any disclaimer, the term of this patent is extended or adjusted under 35 U.S.C. 154(b) by 0 days.

(21) Appl. No.: 14/591,223

(22) Filed: Jan. 7, 2015

(65) Prior Publication Data

US 2015/0270961 A1    Sep. 24, 2015

Related U.S. Application Data

(60) Provisional application No. 61/955,739, filed on Mar. 19, 2014.

(51) Int. Cl.
*H04L 9/06* (2006.01)
*G06Q 10/00* (2012.01)
(Continued)

(52) U.S. Cl.
CPC .............. *G06Q 10/00* (2013.01); *G06F 21/602* (2013.01); *G06Q 20/20* (2013.01); *G06Q 20/382* (2013.01); *G06Q 20/3823* (2013.01);
(Continued)

(58) Field of Classification Search
CPC ...... H04L 63/12; H04L 9/0861; G06F 21/602

USPC ......................................... 713/168, 171, 189
See application file for complete search history.

(56) References Cited

U.S. PATENT DOCUMENTS 6,286,099 B1   9/2001  Kramer
7,386,471 B1   6/2008  Nack
(Continued)

FOREIGN PATENT DOCUMENTS

CN      102387501 A    3/2012
KR      20090039301 A  4/2009

OTHER PUBLICATIONS

International Search Report and Written Opinion mailed Apr. 13, 2015 for related PCT application No. PCT/US15/10405.
(Continued)

*Primary Examiner* — Haresh N Patel
(74) *Attorney, Agent, or Firm* — Morris, Manning & Martin, LLP; John R. Harris; Bryan D. Stewart

(57) ABSTRACT

Systems and methods for creating fingerprints for encryption devices are described herein. In various embodiments, the system includes an encryption device operatively connected to a device management system. According to particular embodiments, the device management system: 1) receives a first payload from the encryption device, the first payload including data in a particular format; 2) creates a fingerprint for the encryption device, the fingerprint including a section format for each of one or more distinct sections of the particular format; 3) storing a record of the fingerprint for the encryption device and the unique identifier at the at least one database; and 4) comparing a format of each subsequent payload received from the encryption device to the fingerprint for the device to determine whether the device has been compromised.

18 Claims, 18 Drawing Sheets

(51) Int. Cl.
*G06Q 20/20* (2012.01)
*G06Q 20/38* (2012.01)
*H04L 29/06* (2006.01)
*G06F 21/60* (2013.01)
*H04L 9/08* (2006.01)

(52) U.S. Cl.
CPC ......... *H04L 9/0861* (2013.01); *H04L 63/0428* (2013.01); *H04L 63/12* (2013.01); *G06Q 2220/00* (2013.01); *G06Q 2220/10* (2013.01); *H04L 2209/24* (2013.01); *H04L 2209/60* (2013.01)

(56) References Cited

U.S. PATENT DOCUMENTS

| | | | |
|---|---|---|---|
| 7,731,435 | B2 | 6/2010 | Piersol et al. |
| 7,941,673 | B1* | 5/2011 | Trimberger ........... H04L 9/0866 326/41 |
| 8,429,041 | B2 | 4/2013 | Bonalle et al. |
| 2002/0082896 | A1 | 6/2002 | Inagi |
| 2003/0035569 | A1* | 2/2003 | Chau ................. G06K 9/00087 382/124 |
| 2003/0051150 | A1* | 3/2003 | Jung .................... H04L 9/3236 713/189 |
| 2005/0166082 | A1 | 7/2005 | Williams et al. |
| 2007/0005974 | A1* | 1/2007 | Kudou ................. G06F 21/606 713/171 |
| 2008/0049644 | A1* | 2/2008 | Halbert .................. H04L 41/12 370/254 |
| 2008/0320317 | A1* | 12/2008 | Funahashi ............... G06F 21/32 713/189 |
| 2010/0306635 | A1* | 12/2010 | Tang .................... H04L 9/0822 714/807 |
| 2010/0325710 | A1* | 12/2010 | Etchegoyen ............ G06F 21/31 726/7 |
| 2010/0325734 | A1* | 12/2010 | Etchegoyen .......... G06F 21/121 726/26 |
| 2010/0332396 | A1* | 12/2010 | Etchegoyen ............ G06F 21/10 705/50 |
| 2010/0332400 | A1* | 12/2010 | Etchegoyen ............ G06F 21/32 705/75 |
| 2011/0093503 | A1* | 4/2011 | Etchegoyen .......... G06F 21/121 707/780 |
| 2011/0093703 | A1* | 4/2011 | Etchegoyen ............ G06F 21/57 713/168 |
| 2011/0196754 | A1 | 8/2011 | Proud et al. |
| 2011/0307710 | A1 | 12/2011 | McGuire et al. |
| 2012/0030209 | A1* | 2/2012 | Bause ................ G06F 17/3002 707/741 |
| 2012/0054050 | A1 | 3/2012 | Ziegler et al. |
| 2012/0084206 | A1 | 4/2012 | Mehew et al. |
| 2012/0324242 | A1 | 12/2012 | Kirsch |
| 2013/0036098 | A1 | 2/2013 | Mutalik et al. |
| 2013/0254117 | A1 | 9/2013 | Von Mueller et al. |
| 2013/0297579 | A1* | 11/2013 | Andrew .................... G06F 8/71 707/698 |
| 2013/0311434 | A1* | 11/2013 | Jones ................ G06F 17/30156 707/692 |
| 2014/0173686 | A1* | 6/2014 | Kgil ...................... H04L 63/205 726/1 |
| 2014/0344921 | A1* | 11/2014 | Hamlin ................... G06F 21/32 726/19 |
| 2015/0220635 | A1* | 8/2015 | Deen ................. G06F 17/30743 707/740 |
| 2015/0220636 | A1* | 8/2015 | Deen .................... H04N 21/222 707/740 |
| 2015/0221336 | A1* | 8/2015 | Deen .................... G11B 27/031 386/290 |

OTHER PUBLICATIONS

International Search Report and Written Opinion mailed Sep. 4, 2015 for related PCT application No. PCT/US2015/21595.
Common Approval Scheme, Point of Interaction Protection Profile, Nov. 26, 2010 Version: 2.0, 161 pages.
Security Standards Council, Payment Card Industry (PCI) PIN Transaction Security (PTS) Point of Interaction (POI), Modular Security Requirements, Version 4.0 Jun. 2013, 59 pages.

* cited by examiner

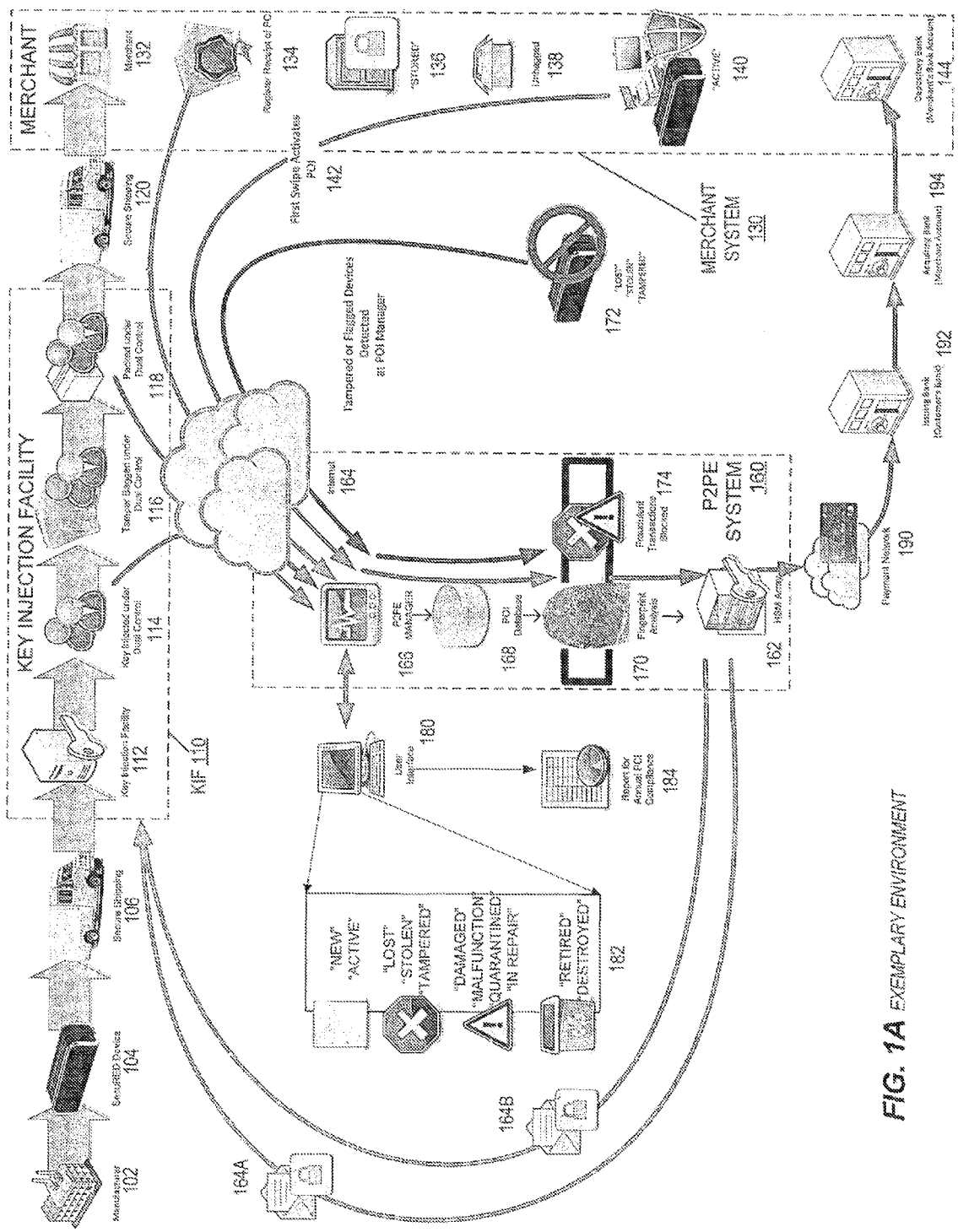
FIG. 1A EXEMPLARY ENVIRONMENT

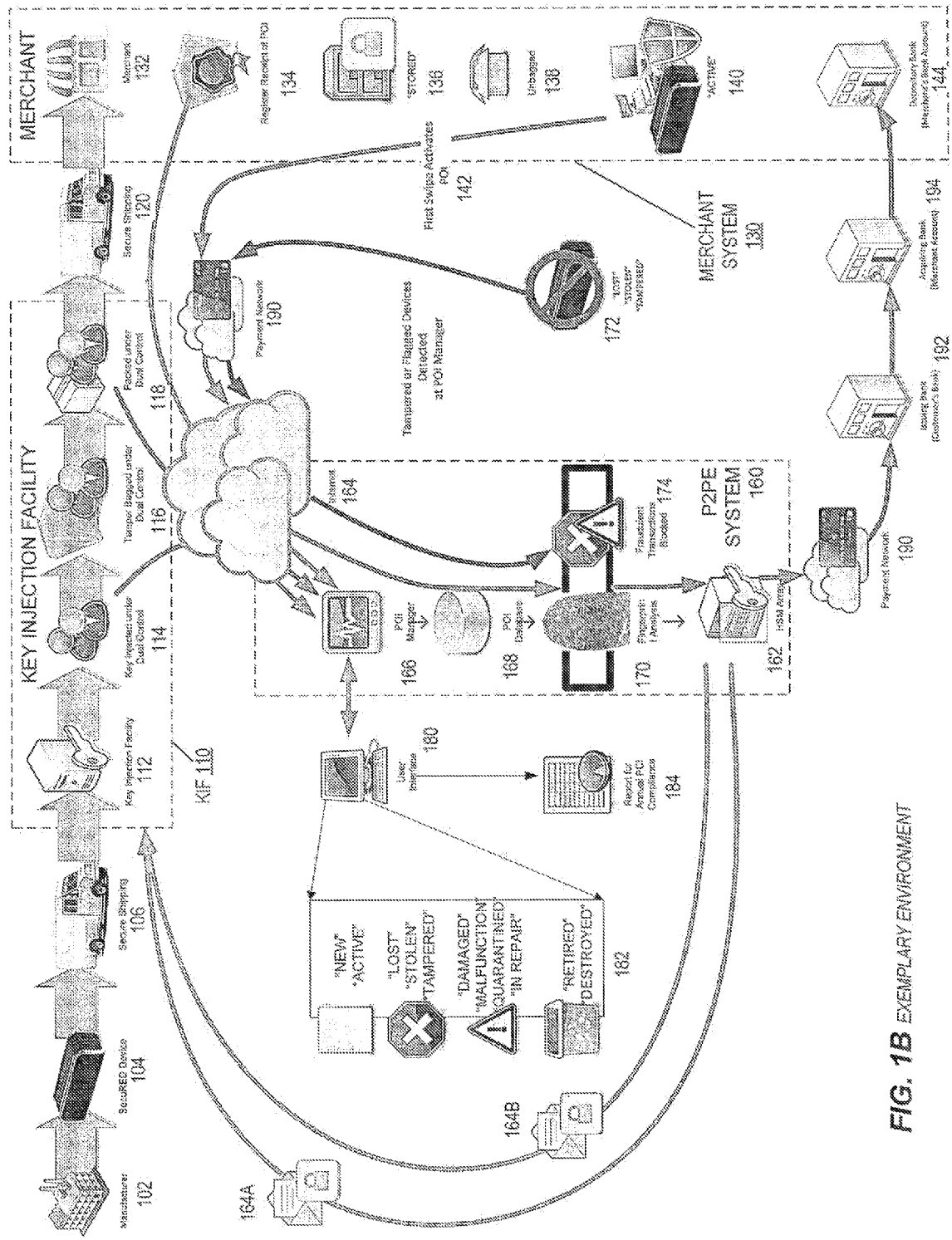
FIG. 1B EXEMPLARY ENVIRONMENT

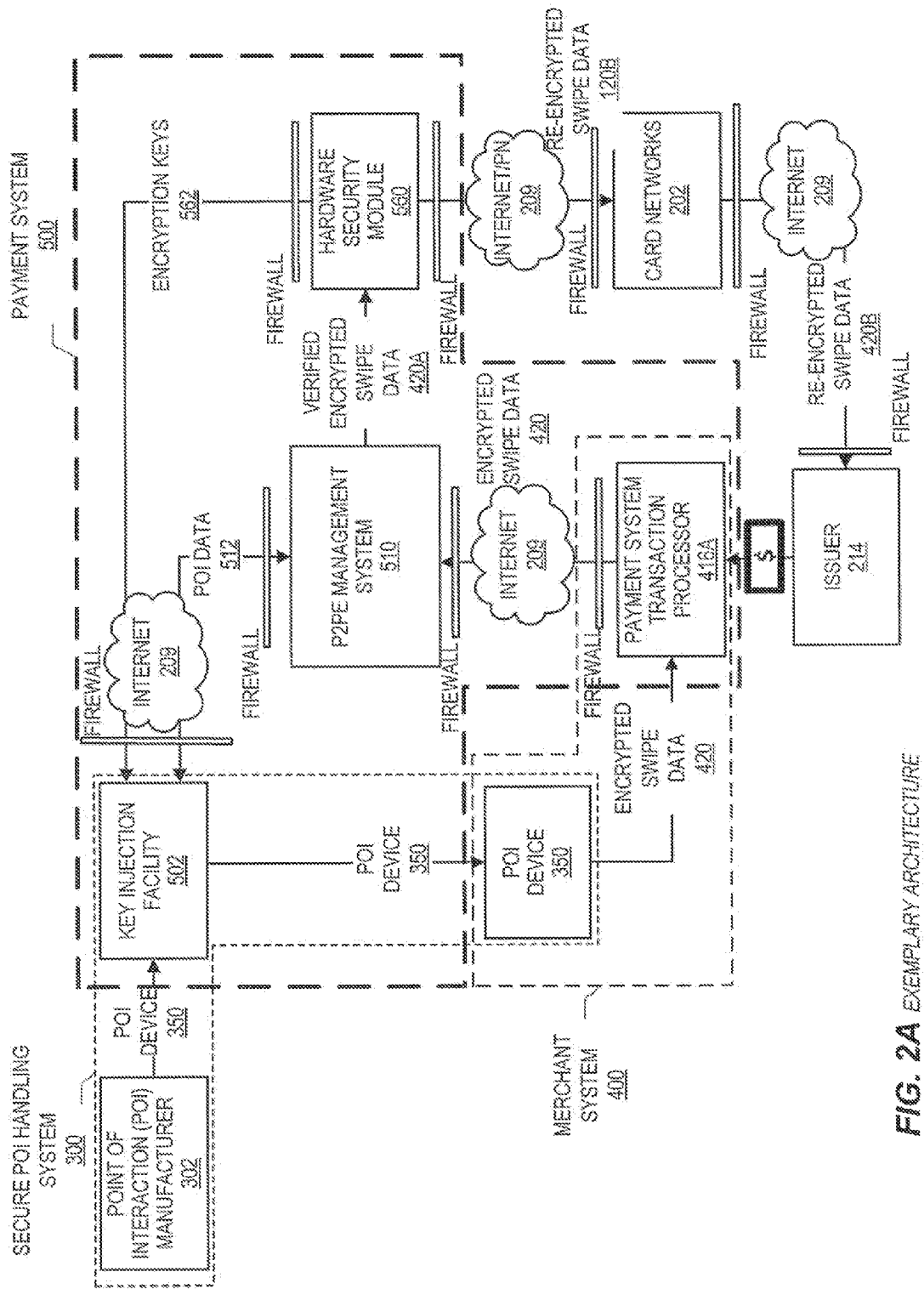
FIG. 2A EXEMPLARY ARCHITECTURE

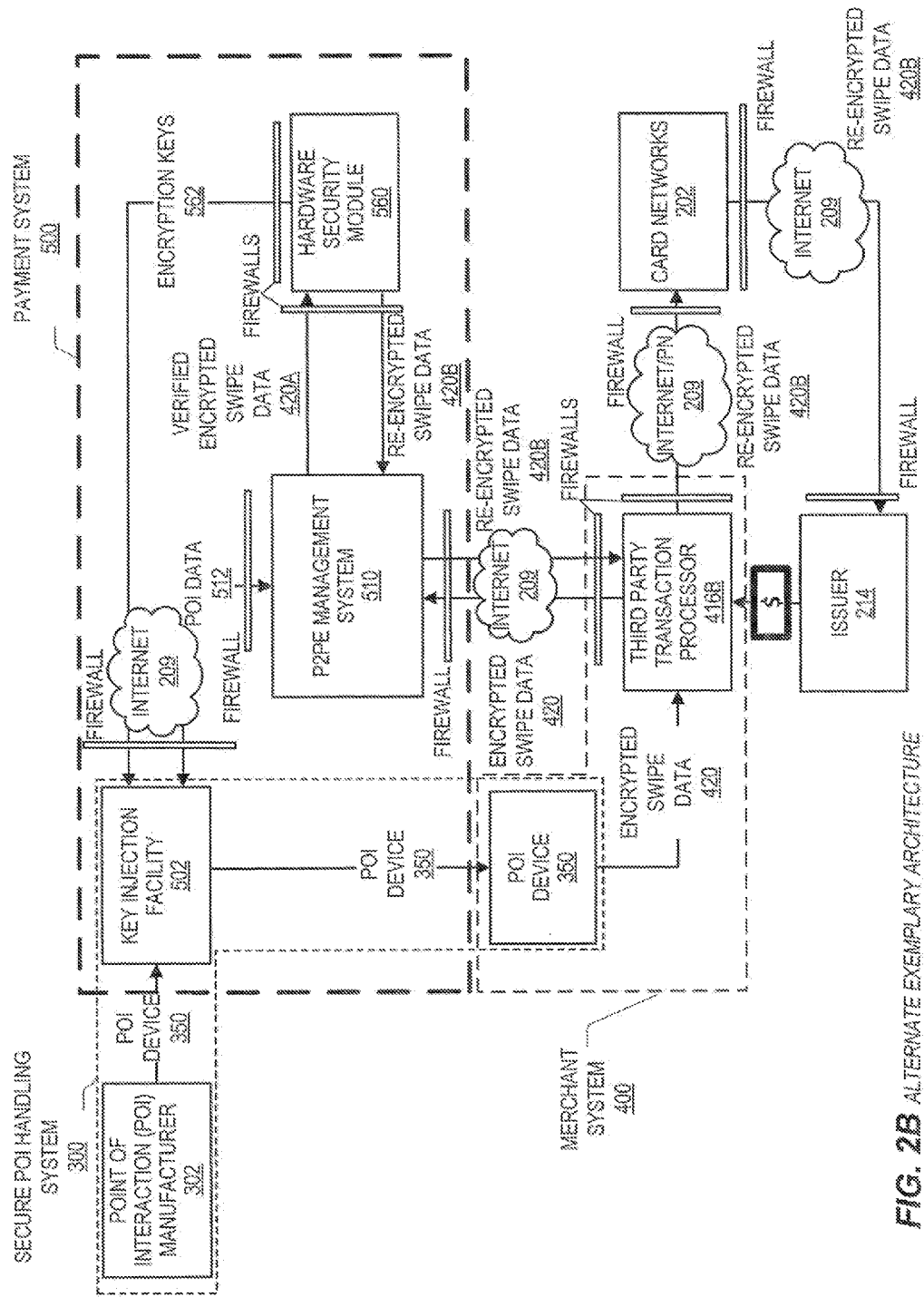
FIG. 2B ALTERNATE EXEMPLARY ARCHITECTURE

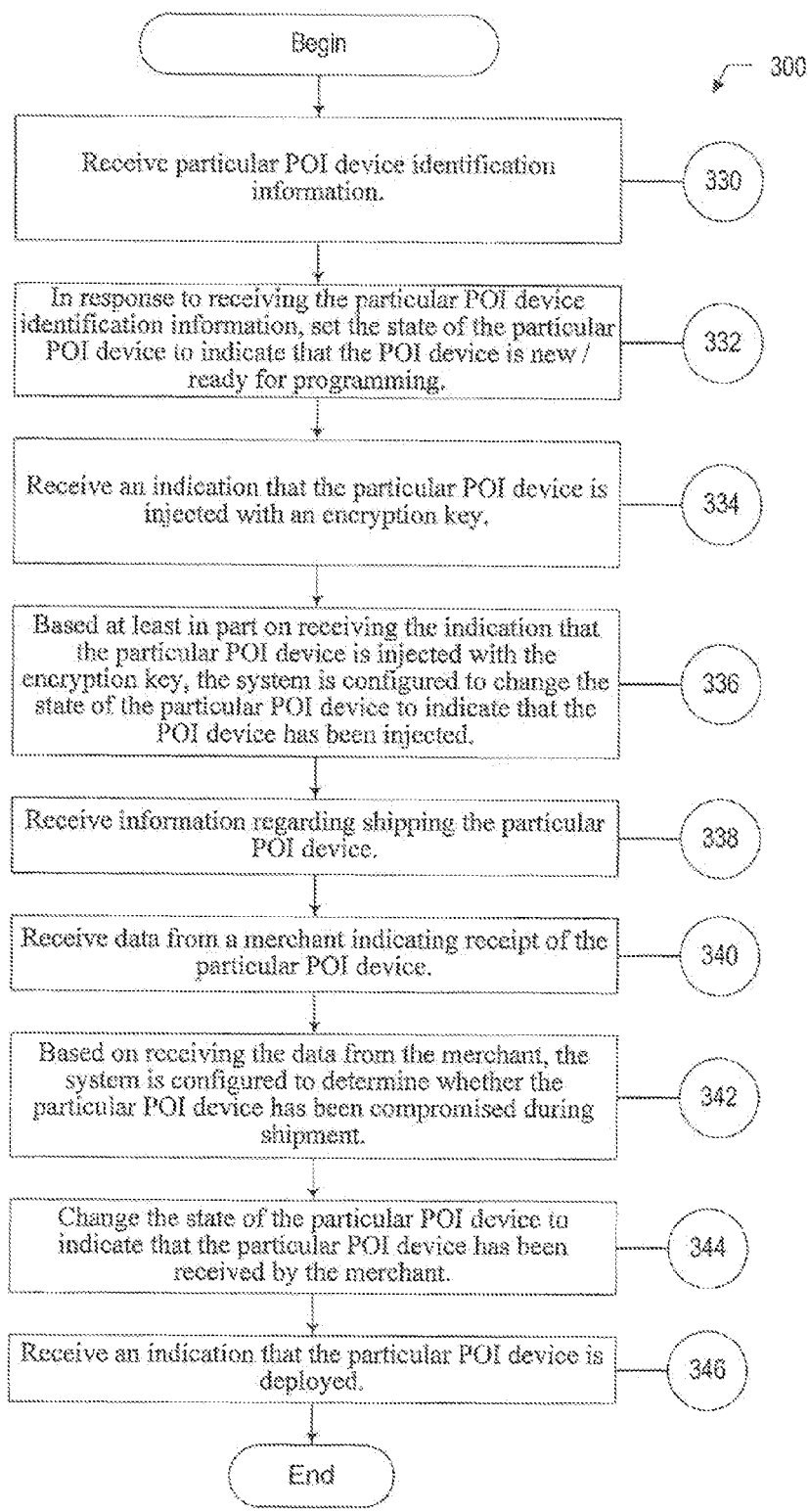
FIG. 3 EXEMPLARY POI HANDLING PROCESS

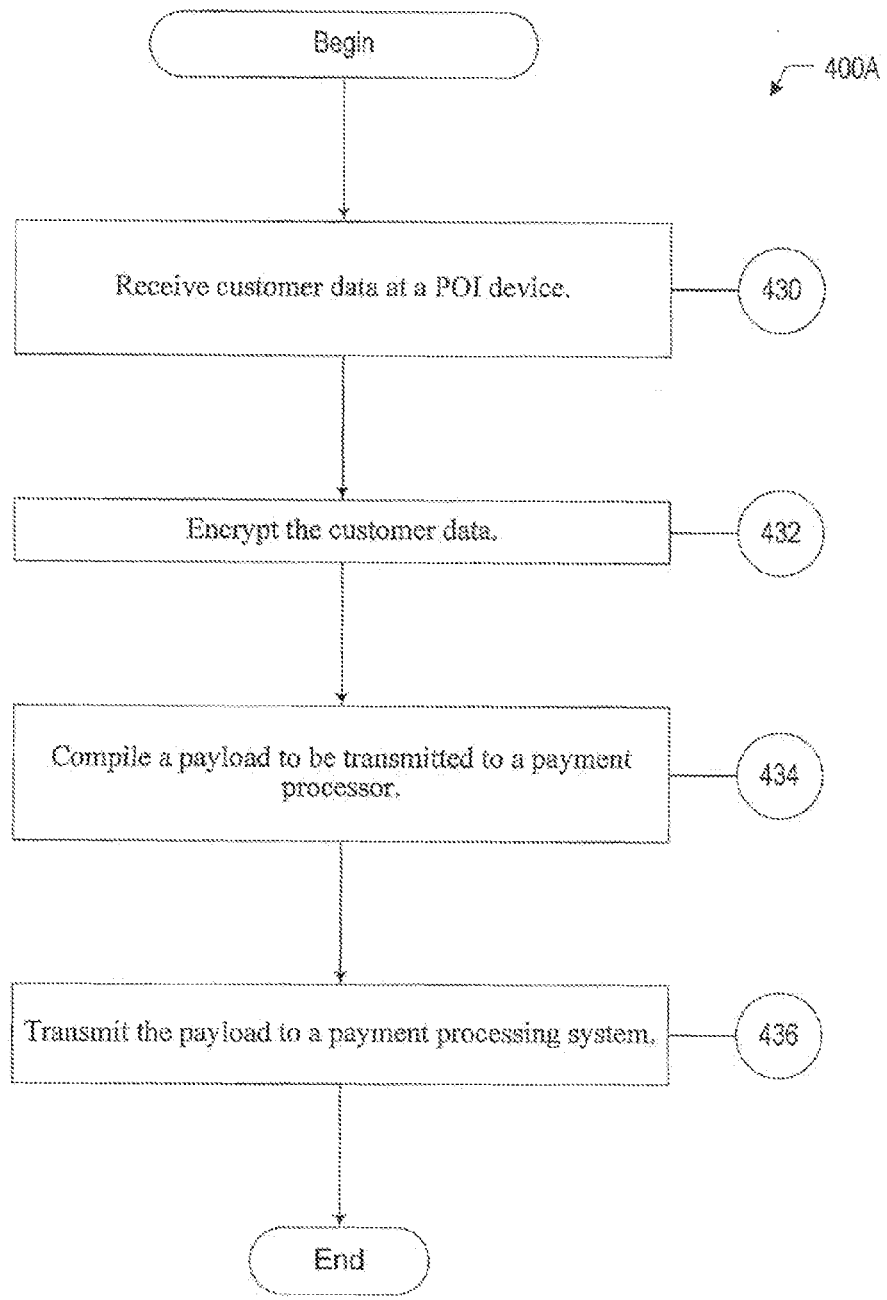
FIG. 4A  MERCHANT DATA PROCESS

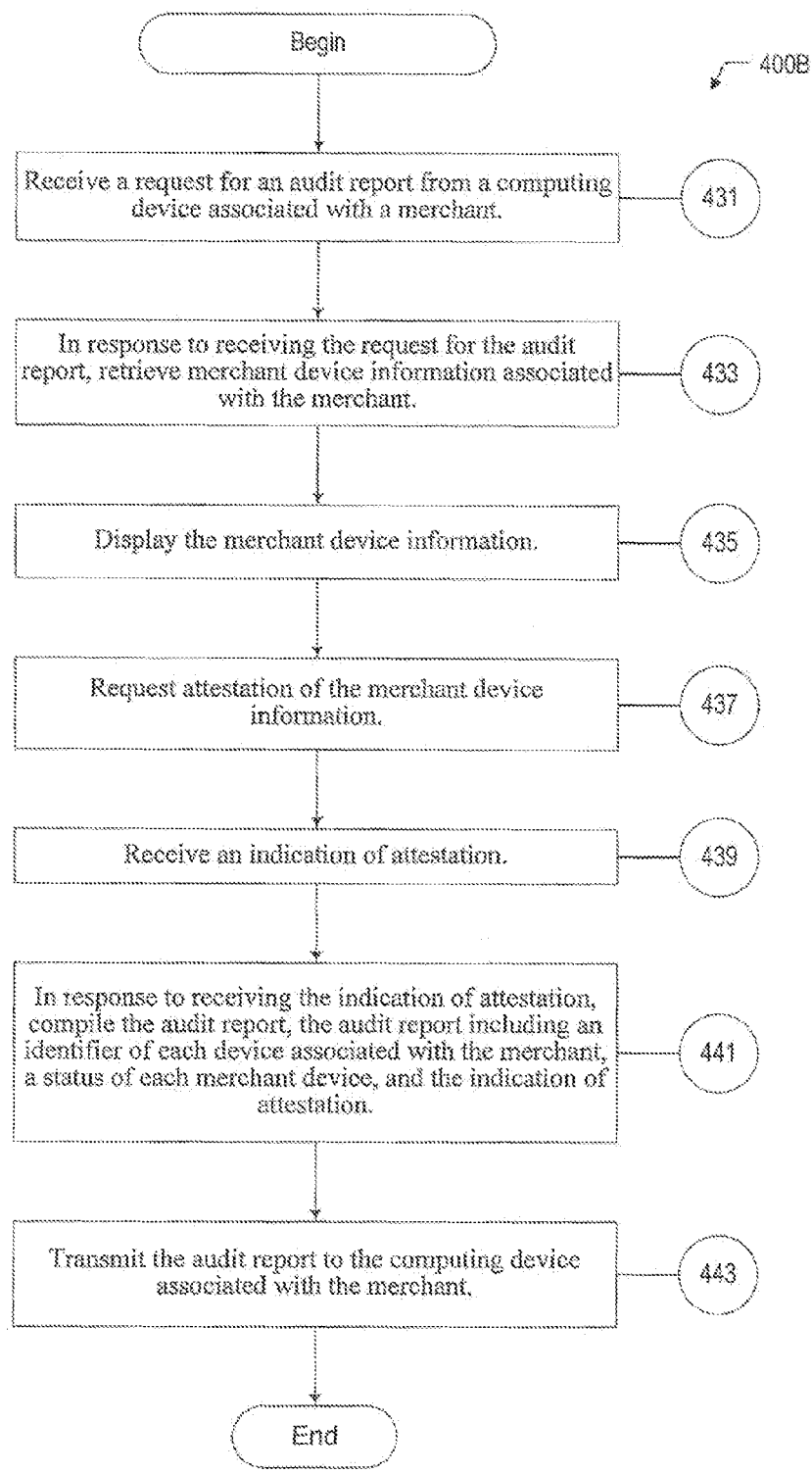
FIG. 4B  P2PE REPORT PROCESS

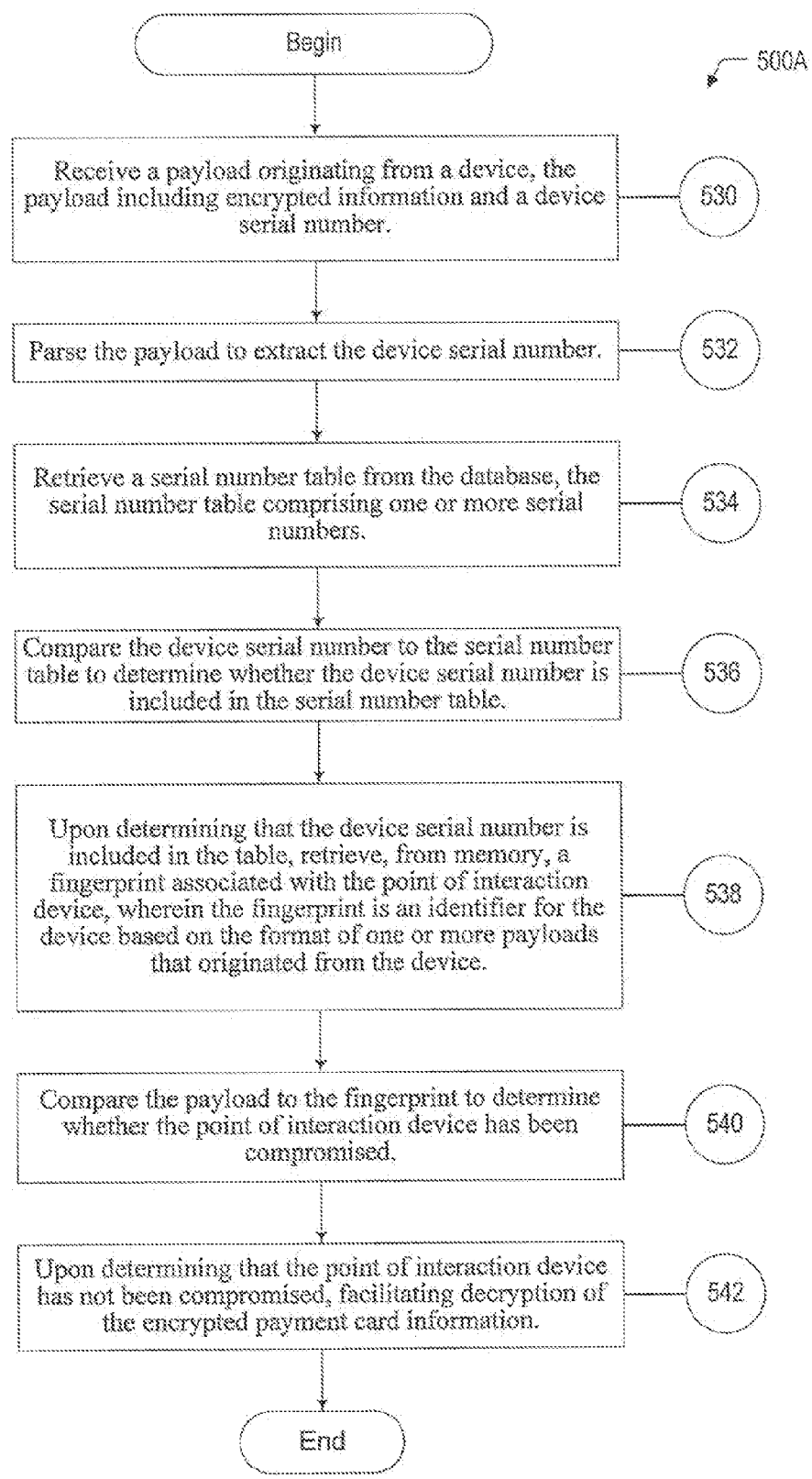
FIG. 5A   EXEMPLARY DECRYPTION PROCESS

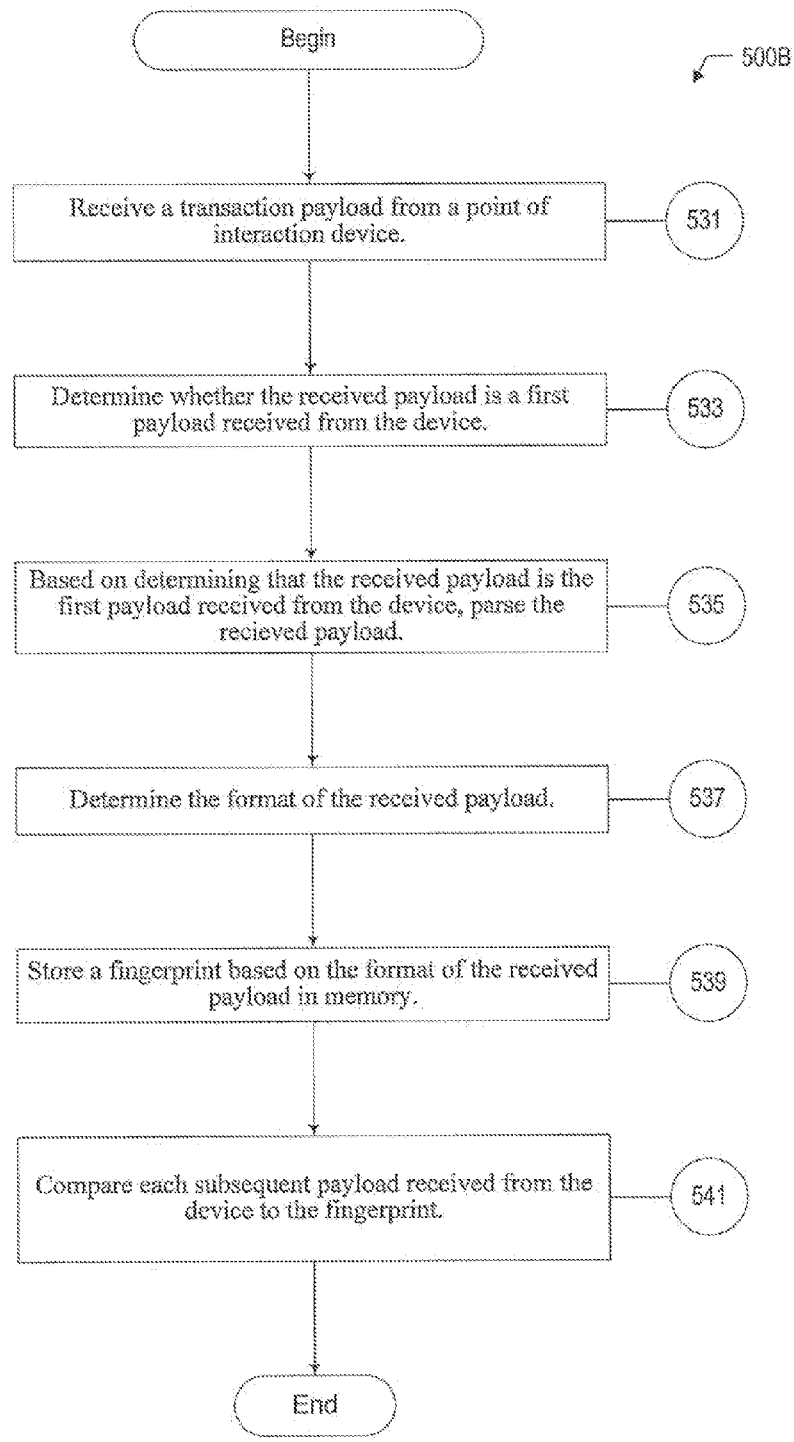
FIG. 5B  EXEMPLARY FINGERPRINT PROCESS

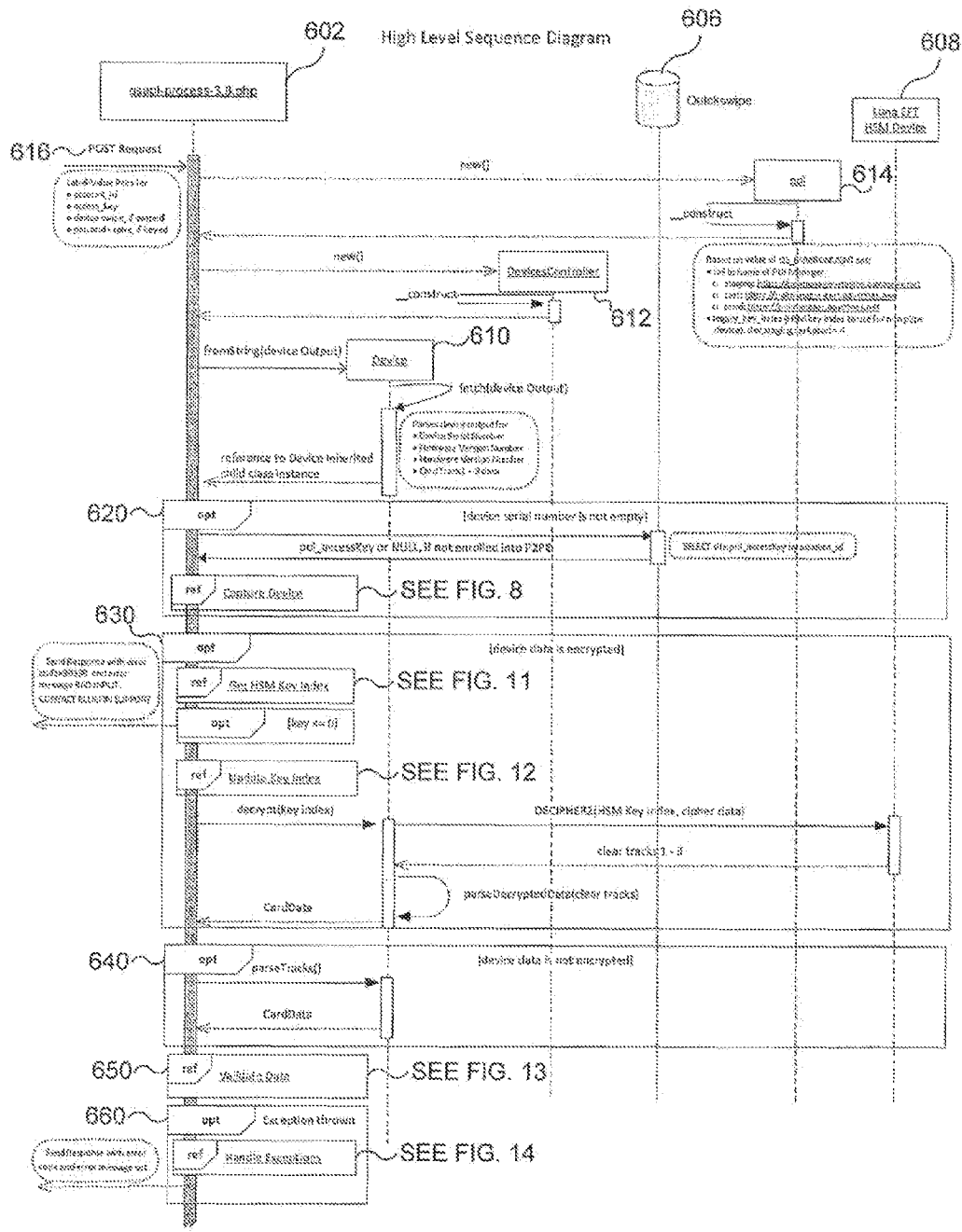
FIG. 6 UML OF EXEMPLARY OVERALL SEQUENCE

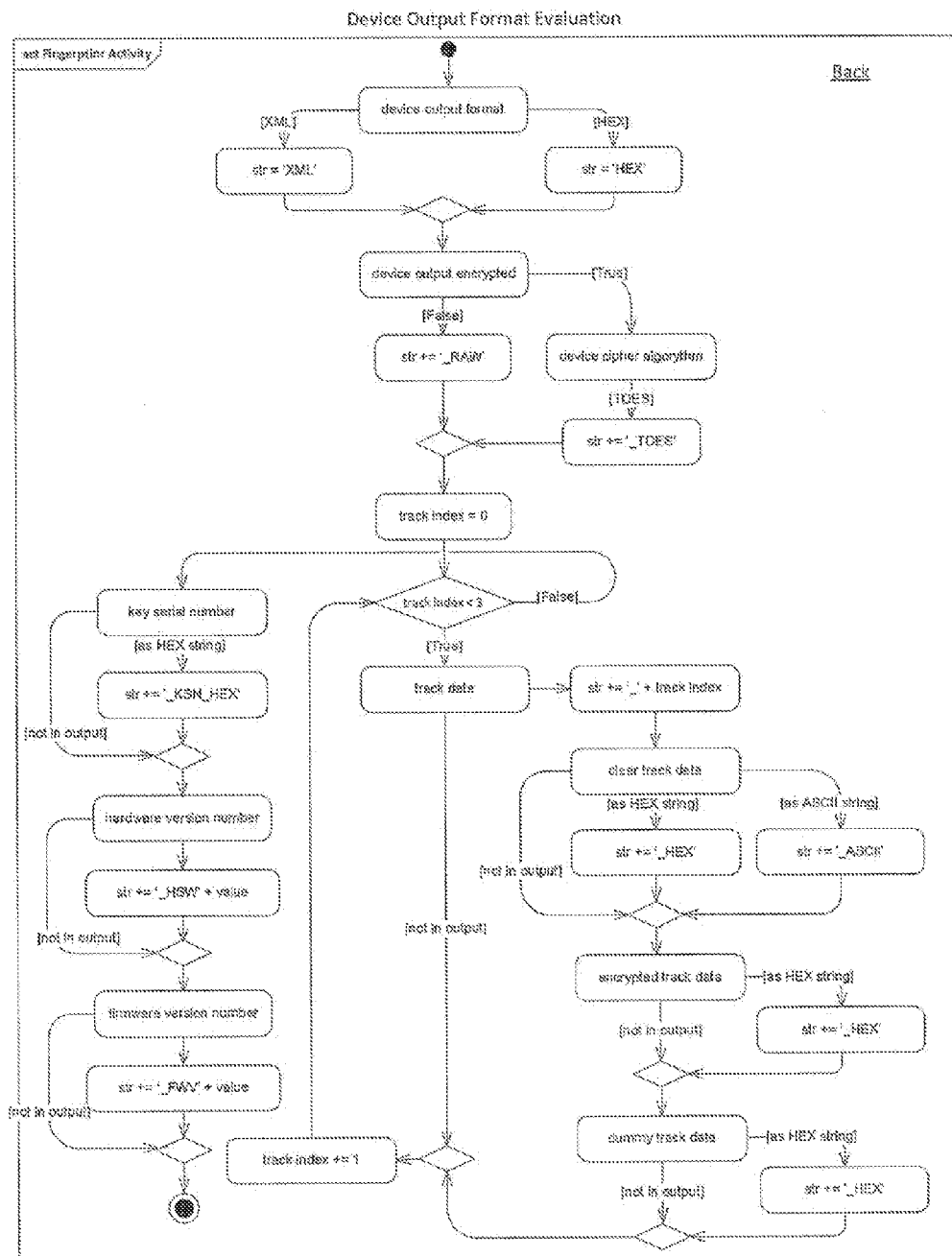
FIG. 7 UML OF EXEMPLARY DEVICE OUTPUT EVALUATION

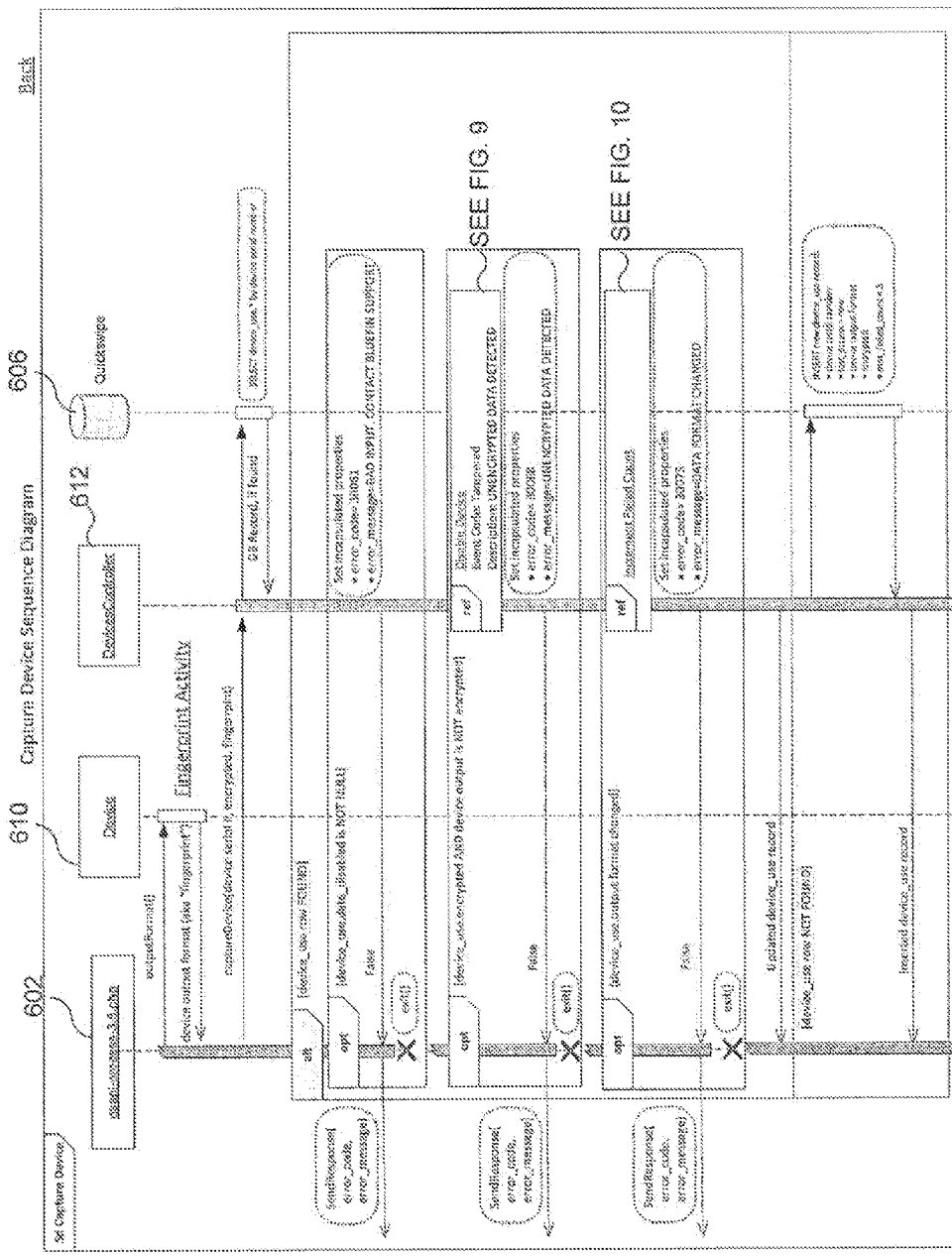
FIG. 8 UML OF EXEMPLARY CAPTURE DEVICE SEQUENCE

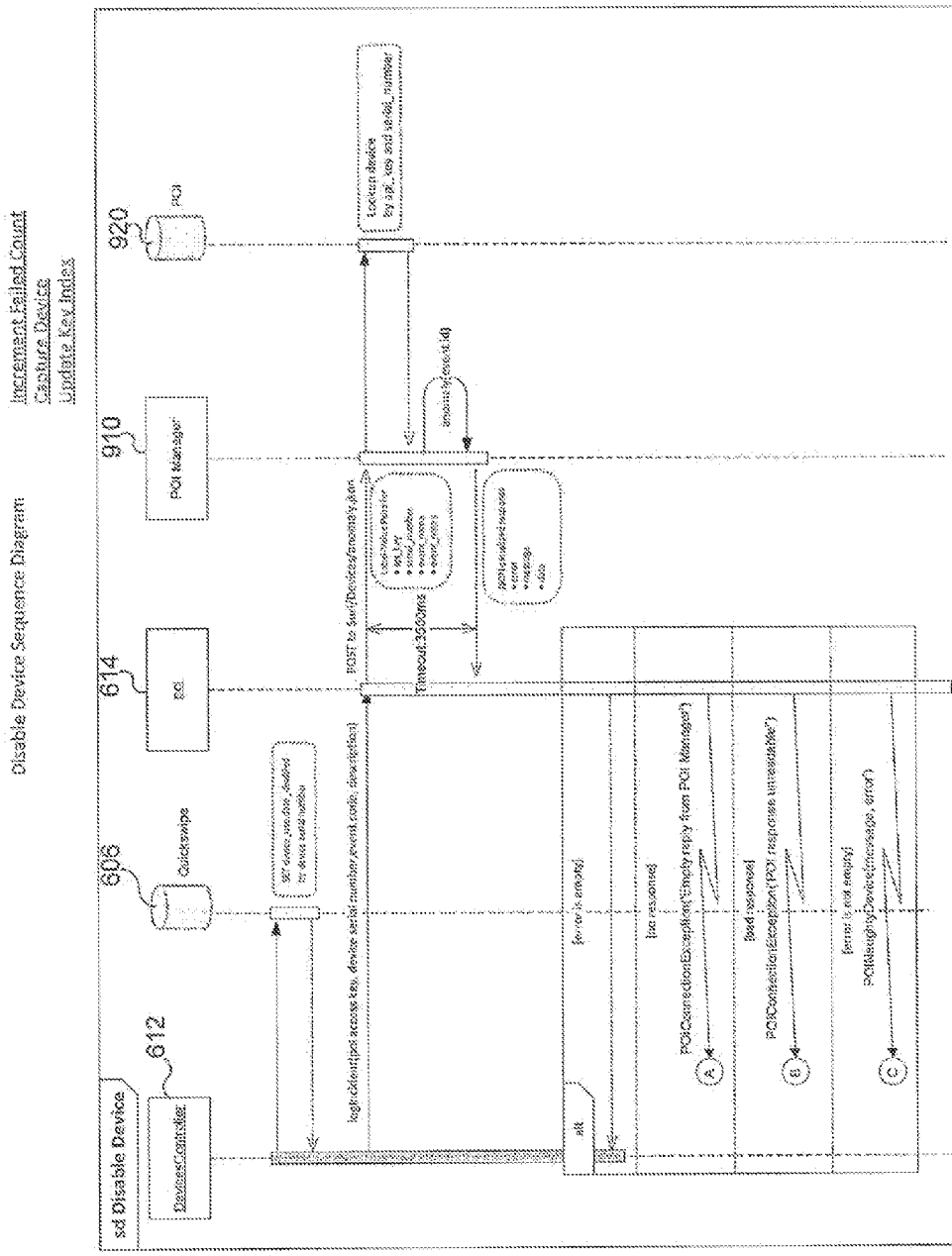
FIG. 9 UML OF EXEMPLARY DEVICE SEQUENCE

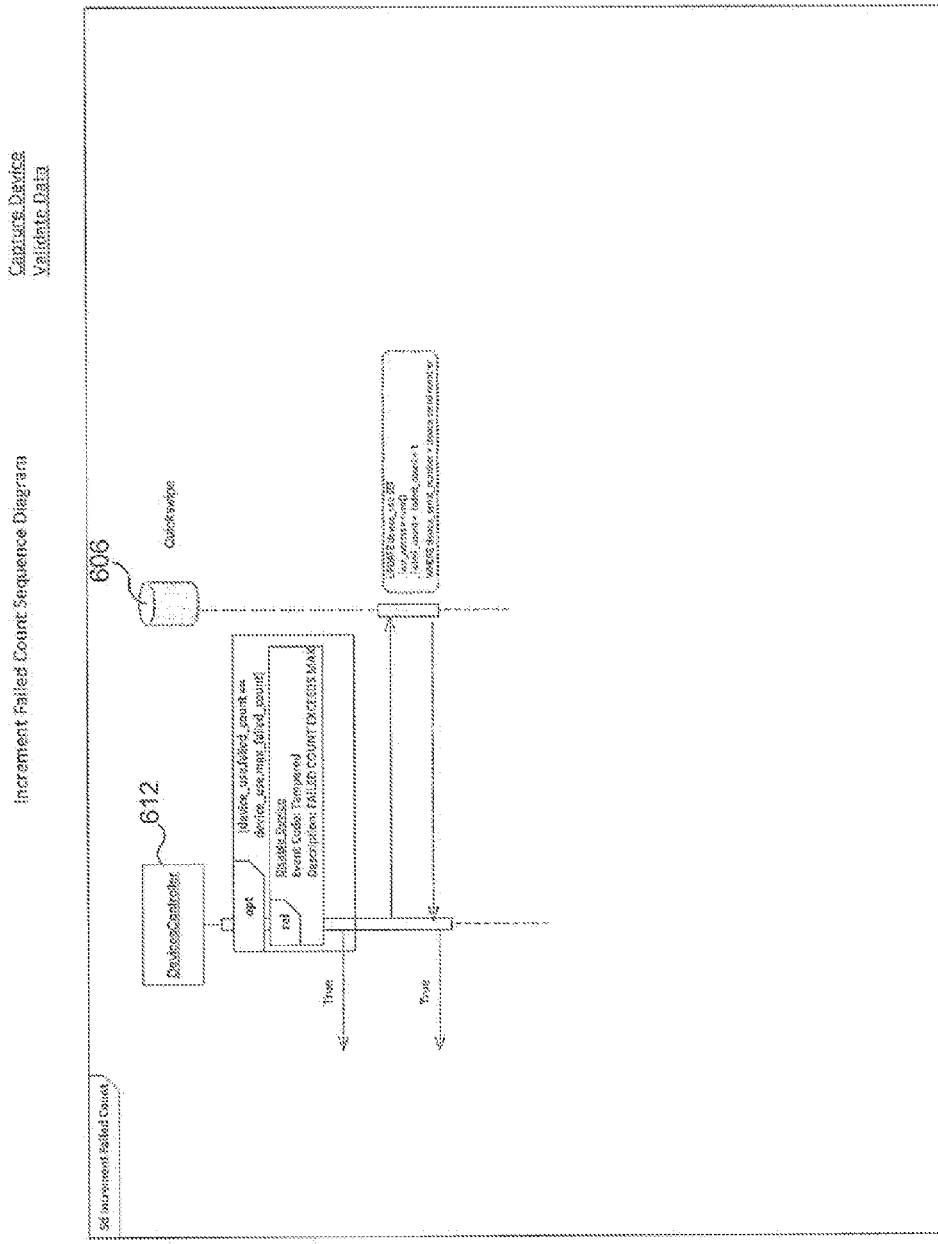
FIG. 10 UML OF EXEMPLARY FAILED COUNT SEQUENCE

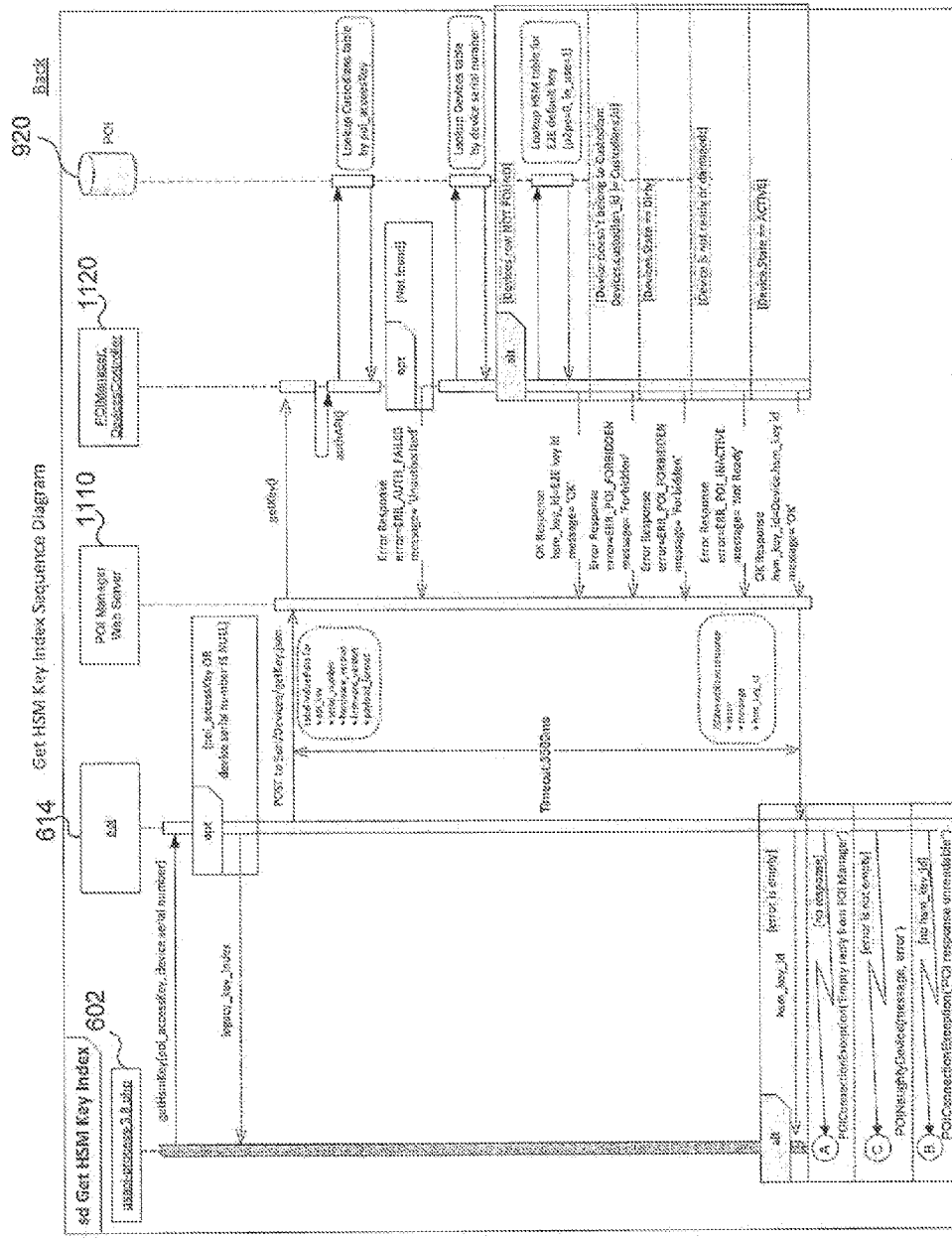
FIG. 11 UML OF EXEMPLARY HSM KEY INDEX SEQUENCE

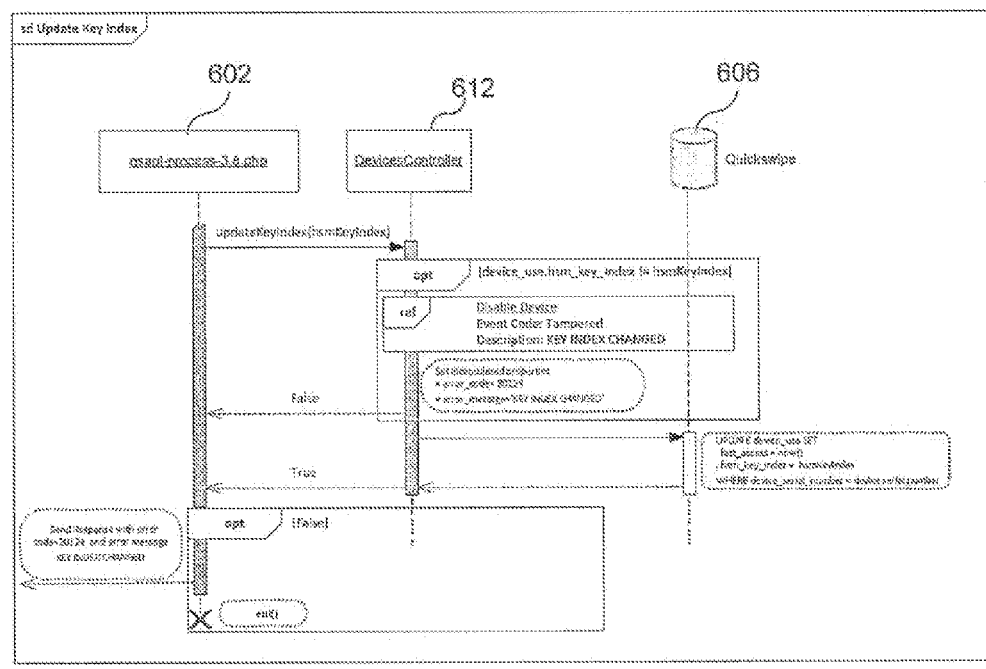
*FIG. 12* UML OF EXEMPLARY UPDATE KEY INDEX SEQUENCE

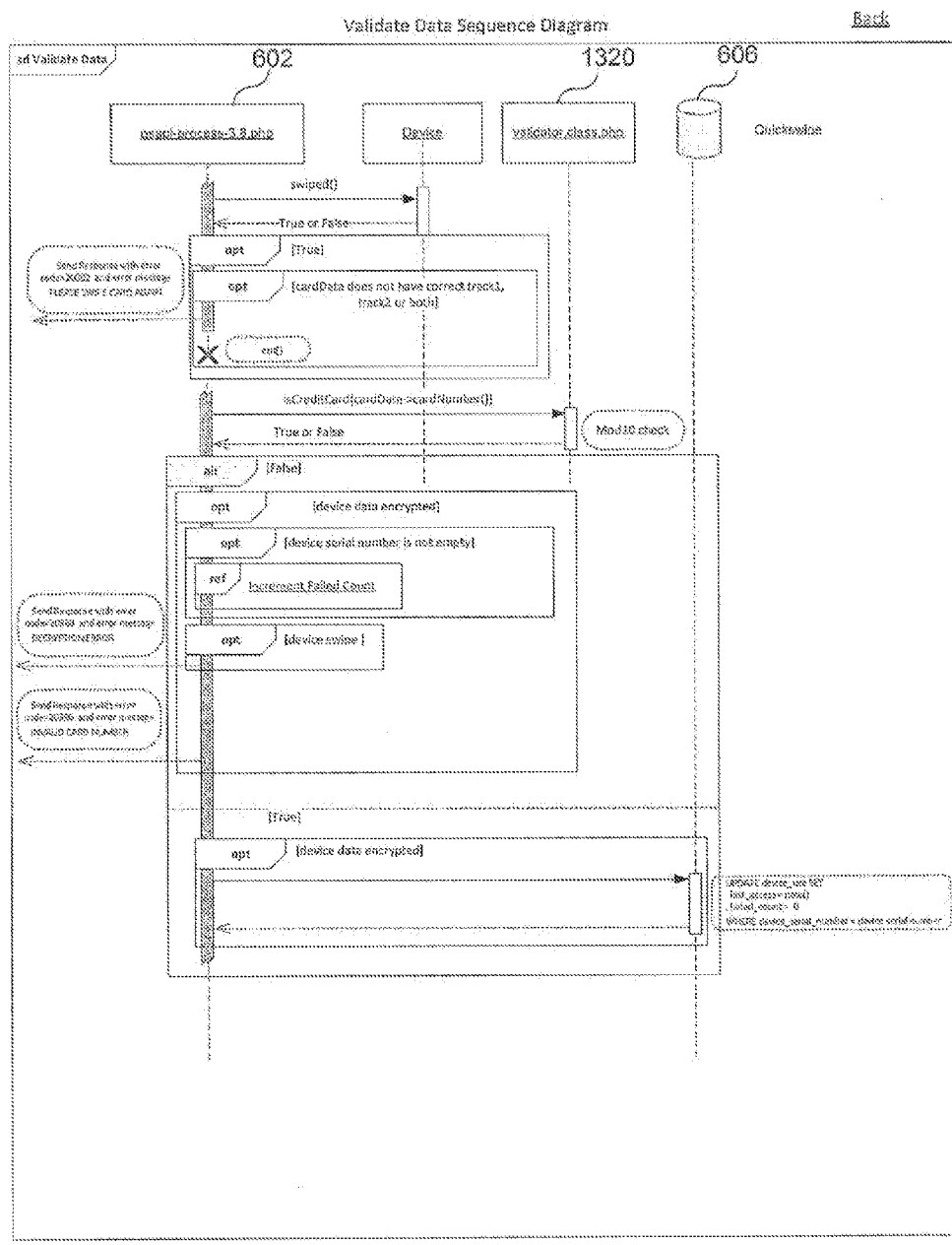
*FIG. 13* UML OF EXEMPLARY VALIDATION SEQUENCE

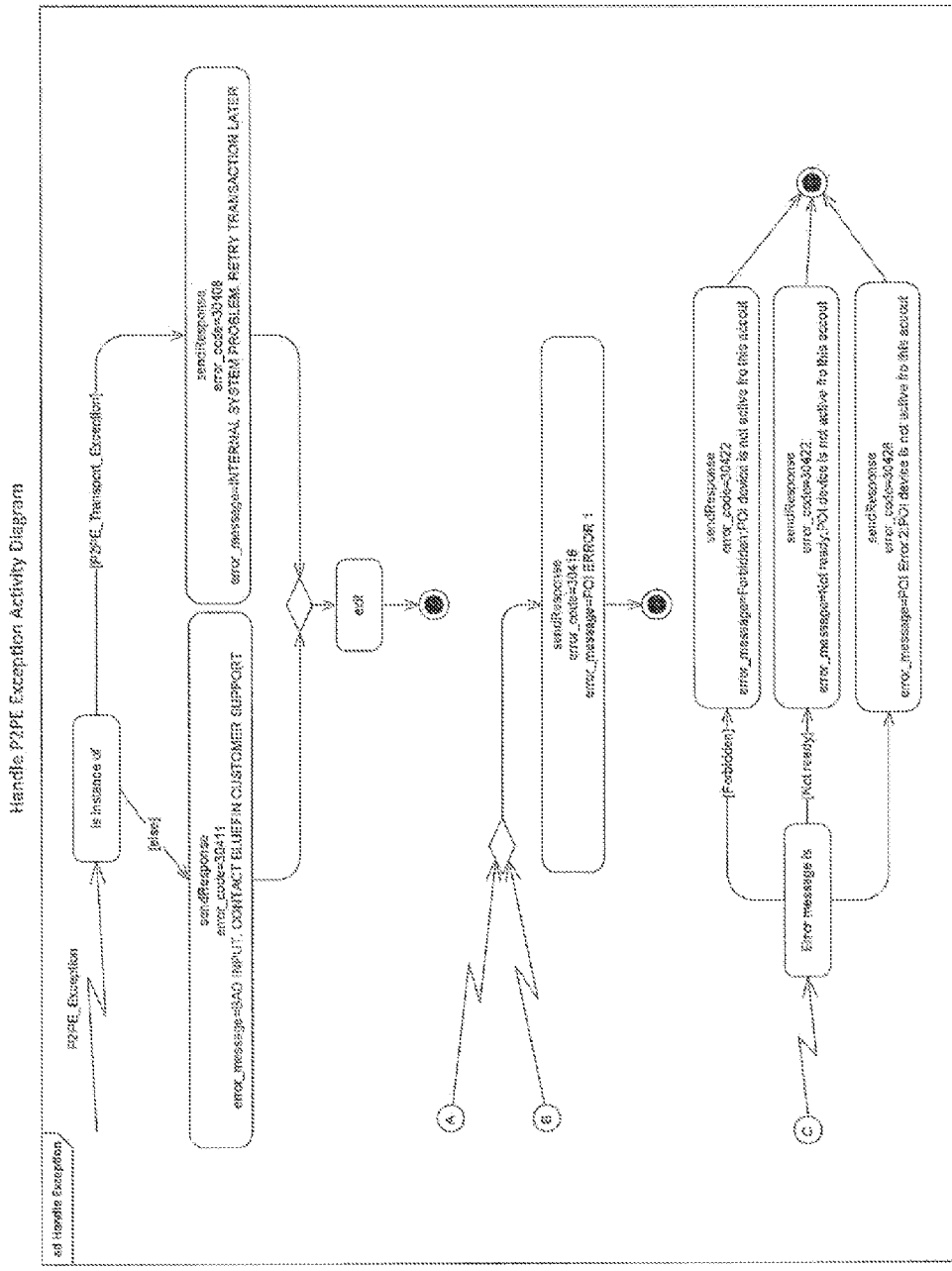
FIG. 14 UML OF EXEMPLARY P2PE EXCEPTION SEQUENCES

SYSTEMS AND METHODS FOR CREATING FINGERPRINTS OF ENCRYPTION DEVICES

CROSS-REFERENCE TO RELATED APPLICATIONS

This application claims the benefit under 35 U.S.C. §119 (e) of U.S. Provisional Patent Application No. 61/955,739, filed Mar. 19, 2014, entitled, "Systems and Methods of Point of interaction Management," incorporated herein by reference in its entirety.

This application is related to and incorporates by reference herein the following U.S. and international (PCT) patent applications:
U.S. patent application Ser. No. 14/591,171, filed Jan. 7, 2015, entitled "Systems and Methods for Facilitating Decryption of Payloads Received from Encryption Devices"; and
U.S. patent application Ser. No. 14/591,218, filed Jan. 7, 2015, entitled "Systems and Methods for Creating and Tracking States of Encryption Devices"; and
International Patent Application No PCT/US2015/010405, filed Jan. 7, 2015 entitled "Systems and Methods for Creating Fingerprints of Encryption Devices".

TECHNICAL FIELD

The present disclosure relates generally point to point encryption (P2PE) and management of point to point encryption systems.

BACKGROUND

Protecting cardholder data during an electronic payment transaction is vital for all entities involved in the processing of that transaction. It was recently made public that in the fourth quarter of 2013 and throughout 2014, significant data breaches occurred at major national retailers. In each instance, cardholder account numbers, and associated cardholder personal data, were illegally obtained by malicious fraudsters, exposing millions of sensitive payment records to potential fraudulent use, including identity theft. As a result, each retailer experienced damages in terms of lost sales, fines, and potential lawsuits for alleged negligence with regard to payment security standards. Another serious consequence of such breaches is brand erosion.

Data breaches are not a new occurrence in the payments industry, but the increasing number of breaches that occur each year, their severity in terms of numbers of records obtained, and the speed and stealth with which such breaches occur is new.

It is not a matter of if a business will experience a breach, it's a matter of when. While it is impossible to eliminate the possibility of a data breach occurring, it is now possible to protect cardholder data integrity in the event of a breach through PCI-validated point-to-point encryption (P2PE). PCI-validated P2PE renders any potential cardholder data useless and void of value in the event of a data theft because the cardholder data cannot be decrypted.

BRIEF SUMMARY OF THE DISCLOSURE

In various embodiments, the systems and methods herein include a point to point encryption management system configured to receive information from a plurality of point of interaction devices, the point to point encryption management system including a) a database for storing device information and b) at least one processor operatively coupled to the database, the at least one processor configured for: 1) receiving a payload originating from a point of interaction device, the payload including encrypted payment information and a device identifier; 2) parsing the payload to extract the device identifier; 3) retrieving an identifier table from the database, the identifier table including one or more device identifiers received by the point to point encryption management system; 4) comparing the device identifier to the identifier table to determine whether the device identifier is included in the identifier table; and 5) upon determining that the device identifier is included in the identifier table, facilitating decryption of the encrypted payment information.

According to particular embodiments, the systems and methods herein include a point to point encryption management system configured to receive information from a plurality of point of interaction devices, the point to point encryption management system including a) a database for storing device information and b) at least one processor operatively coupled to the database, the at least one processor configured for: 1) receiving a payload originating from a point of interaction device, the payload including encrypted data and a device serial number; 2) parsing the payload to extract the device serial number; 3) retrieving a serial number table from the database, the serial number table including one or more serial numbers received by the point to point encryption management system; 4) comparing the device serial number to the serial number table to determine whether the device serial number is included in the serial number table; 5) upon determining that the device serial number is included in the table, retrieving, from memory, a fingerprint associated with a record of the point of interaction device, wherein the fingerprint is an identifier created by the point to point encryption management system for the point of interaction device based on the format of one or more payloads that originated from the point of interaction device; 6) comparing the payload to the fingerprint to determine whether the point of interaction device has been compromised; and 7) upon determining that the point of interaction device has not been compromised, facilitating decryption of the encrypted payment card information.

In one or more embodiments, the systems and methods herein include a computer-implemented method for decrypting encrypted data, the computer-implemented method including: A) providing at least one encryption device including at least one processor configured to transmit encrypted data and a device serial number; and B) providing an encryption management system configured to receive information from the encryption device and at least one computer terminal located at a key injection facility, the encryption management system including a) a database for storing device information and b) at least one processor operatively coupled to the database, the at least one processor configured for: 1) receiving an initial device serial number from the at least one terminal located at the key injection facility; 2) writing the initial device serial number to a table in memory and storing the table in a database; 3) receiving a payload at least partially originating from the encryption device, the payload including encrypted data and the device serial number; 4) parsing the payload to extract the device serial number; 5) retrieving the table from the database; 6) comparing the device serial number to the initial device serial number to determine whether the device serial number is included in the table; and 7) upon determining that the device serial number and the initial device serial number are the same serial number, facilitating decryption of the encrypted data.

According to some embodiments, the systems and methods herein include a computer system for point to point encryption of payment transactions, the computer system including: A) at least one point of interaction device including a) one or more magnetic read heads for reading consumer payment cards and b) at least one processor configured to transmit consumer payment card information and a device serial number associated with the at least one point of interaction device; B) a hardware security module configured for decryption of payment card information; and C) a point to point encryption management system configured to receive information from the point of interaction device and at least one computer terminal located at a key injection facility, the point to point encryption management system including a) a database for storing device information and b) at least one processor operatively coupled to the database, the at least one processor configured for: 1) receiving an initial device serial number from the at least one computer terminal located at the key injection facility; 2) writing the initial device serial number to a table in memory and storing the table in the database; 3) receiving a first payload originating from the point of interaction device, the first payload including first encrypted payment card information and the device serial number; 4) parsing the payload to extract the device serial number; 5) retrieving the table from the database; 6) comparing the device serial number to the initial device serial number to determine whether the device serial number is included in the table; 7) upon determining that the device serial number and the initial device serial number are the same serial number: i) facilitating decryption of the payment card information; and ii) creating a fingerprint for the point of interaction device based on the format of the first payload and storing the payload identifier in memory; 8) receiving a second payload originating from the point of interaction device including encrypted second payment card information and the device serial number; 9) parsing the received second payload to extract the device serial number; 10) retrieving the table from the database; 11) comparing the device serial number to the initial device serial number to determine whether the device serial number is included in the table; 12) upon determining that the device serial number and the initial device serial number are the same serial number, retrieving the fingerprint; 13) comparing the second payload to the fingerprint to determine whether the point of interaction device has been compromised; and 14) upon determining that the point of interaction device has not been compromised, transmitting the second payment information to the hardware security module for decryption.

In at least one embodiment, the systems and methods herein include a computer system decrypting payment transactions, the computer system including: A) at least one point of interaction device including one or more processors configured to transmit consumer payment card information and a device serial number associated with the at least one point of interaction device; and B) a point to point encryption management system configured to receive information from the point of interaction device and at least one computer terminal located at a key injection facility, the point to point encryption management system including a) a database for storing device information and b) at least one processor operatively coupled to the database, the at least one processor configured for: 1) receiving an initial device serial number from the at least one computer terminal located at the key injection facility; 2) writing the initial device serial number to a table in memory and storing the table in the database; 3) receiving a payload at least partially originating from the point of interaction device, the payload including encrypted payment card information and the device serial number; 4) parsing the payload to extract the device serial number; 5) retrieving the table from the database; 6) comparing the device serial number to the initial device serial number to determine whether the device serial number is included in the table; and 7) upon determining that the device serial number and the initial device serial number are the same serial number, facilitating decryption of the payment card information.

In further embodiments, the systems and methods herein include a computer-implemented method for decrypting payment transactions, the method including: 1) providing at least one point of interaction device including one or more processors configured to transmit consumer payment information and a device serial number associated with the at least one point of interaction device; 2) providing a point to point encryption management system configured to receive information from the point of interaction device, the point to point encryption management system including a) a database for storing device information and b) at least one processor operatively coupled to the database; 3) receiving, by the least one processor, an initial device serial number at least one computer third party computing device; 4) writing, by the least one processor, the initial device serial number to a table in memory and storing the table in the database; 5) receiving, by the at least one processor, a payload at least partially originating from the point of interaction device, the payload including encrypted payment information and the device serial number; 6) parsing, by the at least one processor, the payload to extract the device serial number; 7) comparing, by the at least one processor, the device serial number to the initial device serial number to determine whether the device serial number and the initial serial number are the same serial number; and 8) upon determining that the device serial number and the initial device serial number are the same serial number, facilitating decryption of the payment information.

According to various embodiments, the systems and methods herein include a computer system for creating a fingerprint for a device, the computer system including the device operatively connected to a device management system, the device management system including at least one processor operatively coupled to at least one database, the at least one processor configured for: 1) receiving a first payload from the device, the first payload including data in a particular format and a device indicator, the device indicator including a unique identifier used for identifying the device; 2) creating the fingerprint for the device, the fingerprint including a section format for each of one or more distinct sections of the particular format in a particular order; 3) storing a record of the fingerprint for the device and the unique identifier at the at least one database; and 4) comparing a format of each subsequent payload received from the device to the fingerprint for the device to determine whether the device has been compromised.

In particular embodiments, the systems and methods herein include a computer system for creating a fingerprint for a device, the computer system including the device operatively connected to a device management system, the device management system including at least one processor operatively coupled to at least one database, the at least one processor configured for: 1) receiving payloads from a particular device, each payload including encrypted and unencrypted data in a format; 2) comparing the format of each payload from the particular device to the fingerprint associated with the particular device; and 3) upon determining that the format of a particular payload of the payloads received from the particular device does not match the fingerprint associated with the particular device, declining to decrypt the encrypted data of the particular payload and transmitting a notification of declining to decrypt the encrypted data to a user computing system associated with a user.

According to one or more embodiments, the systems and methods herein include a computer-implemented method for creating a fingerprint for a device, the method including: A) providing a device capable of encrypting data; B) providing a computer system operatively coupled to the device, the computer system including: 1) a decrypting means for decrypting data received from the device; 2) a fingerprint creation means for creating a fingerprint associated with the device; 3) at least one database; and 4) at least one processor operatively coupled to the decrypting means, the fingerprint creation means, and the at least one database; C) receiving, by the at least one processor, a first payload from the device, the first payload including data in a particular format, a device indicator, and encrypted data, the device indicator including a unique identifier used for identifying the device; D) creating, by the fingerprint creation means, a fingerprint for the device, the fingerprint including a section format for each of one or more distinct sections of the particular format in a particular order; E) storing a record of the fingerprint for the device and the unique identifier at the at least one database and changing a state of the device to active by the at least one processor; F) comparing, by the at least one processor, a second particular format of a subsequent payload received from the device to the fingerprint for the device to determine whether the device has been compromised; and G) upon determining that the device has not been compromised, decrypting, by the decrypting means, encrypted data of the subsequent payload.

In at least one particular embodiment, the systems and methods herein include computer system for managing encryption device status changes including a P2PE management system including at least one processor and operatively connected to an encryption device, the at least one processor configured for changing a state of the encryption device based upon transactional information received from the encryption device, wherein changing the state of the encryption device based upon transaction information includes: 1) receiving a transaction payload from an encryption device, the transaction payload including transaction information and non-transaction information; 2) determining whether the transaction information is unencrypted; and 3) in response to determining that the transaction information is unencrypted, disabling the encryption device by changing a state of the encryption device to a tampered state.

In further embodiments, the systems and methods herein include a computer-implemented method for managing encryption device status changes, the method including the steps of: A) providing a P2PE management system including at least one processor and operatively connected to an encryption device; and B) changing, by the at least one processor, a state of the encryption device based upon transactional information received from the encryption device, wherein changing the state of the encryption device based upon transaction information includes: 1) receiving a transaction payload from an encryption device, the transaction payload including transaction information and non-transaction information; 2) determining whether the transaction information is unencrypted; and 3) in response to determining that the transaction information is unencrypted, disabling the encryption device by changing a state of the encryption device to a tampered state.

In still further embodiments, the systems and methods herein include a computer system for managing encryption device status changes including a P2PE management system including at least one processor and operatively connected to an encryption device, the at least one processor configured for: A) changing the state of the encryption device based on input from an operator; B) changing a state of the encryption device based upon transactional information received from the encryption device, wherein changing the state of the encryption device based upon transaction information includes: 1) receiving a first transaction payload from an encryption device, the first transaction payload including first transaction information and first non-transaction information; 2) upon receiving the first transaction payload from the encryption device, changing the state of the encryption device from the deployed state to an active state and facilitating decryption of the first transaction information; 3) receiving a second transaction payload from the encryption device, the second transaction payload including second transaction information and second non-transaction information; 4) determining whether the second transaction information is unencrypted; and 5) in response to determining that the second transaction information is unencrypted, disabling the encryption device by changing the state of the encryption device from the active state to a tampered state.

BRIEF DESCRIPTION OF THE DRAWINGS

The accompanying drawings illustrate one or more embodiments and/or aspects of the disclosure and, together with the written description, serve to explain the principles of the disclosure. A number of the diagrams below are unified modeling language (UML) 2.5 Sequence Diagrams. UML sequence diagrams focus on the message interchange between the numbers of lifelines (aka individual participants). One of ordinary skill in the art will understand that UML diagrams are read from left to right and from the top to the bottom. See www.uml-diagrams.org/sequence-diagrams-combined-fragment.html for more information on UML diagrams.

FIG. 1A is an exemplary point to point encryption (P2PE) management system and payments environment according to one embodiment of the present systems and methods.

FIG. 1B is an alternative exemplary P2PE management system and payments environment according to one embodiment of the present systems and methods.

FIG. 2A shows a block diagram of an exemplary architecture of the P2PE management system of FIG. 1A according to one embodiment of the present systems and methods.

FIG. 2B shows a block diagram of an exemplary architecture of the P2PE management system of FIG. 1B according to one embodiment of the present systems and methods.

FIG. 3 is a flow chart illustrating an exemplary point of interaction management process according to one embodiment of the present systems and methods.

FIG. 4A is a flow chart illustrating an exemplary merchant data process according to one embodiments of the present systems and methods.

FIG. 4B is a flow charts illustrating an exemplary P2PE report processes according to one embodiment of the present systems and methods.

FIG. 5A is a flow chart illustrating an exemplary decryption process according to one embodiment of the present systems and methods.

FIG. 5B is a flow chart illustrating an exemplary fingerprint process according to one embodiment of the present systems and methods.

FIGS. 6-14 are UML diagrams illustrating exemplary sequences of the present systems and methods.

DETAILED DESCRIPTION

For the purpose of promoting an understanding of the principles of the present disclosure, reference will now be made to the embodiments illustrated in the figures and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates.

Prior to a detailed description of the disclosure, the following definitions are provided as an aid to understanding the subject matter and terminology of aspects of the present systems and methods, are exemplary, and not necessarily limiting of the aspects of the systems and methods, which are expressed in the claims. Whether or not a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

DEFINITIONS/GLOSSARY

Account Data: may refer to cardholder data and/or sensitive authentication data, such as, but not limited to a PAN, a routing number, a cardholder name, an expiration date, a service code, magnetic stripe data (or chip data), a card security code (e.g., CAV2, CVC2, CVV2, CID, etc.), one or more personal identification (PIN) numbers, and/or PIN blocks.

Bank: any suitable banking entity that may issue one or more cards (e.g., credit cards, debit cards, etc.) to a consumer, may receive deposits (e.g., from a merchant), manage accounts for customers, etc.

Fingerprint or Device Fingerprint: in various embodiments, a set of information used to identify a particular device, wherein the set of information may be based on the particular device's one or more attributes. In at least one embodiment, the set of information is for a POI Device and includes a serial number associated with the POI Device.

Hardware Security Module (HSM): a device that, in various embodiments, safeguards, houses, and manages digital encryption and decryption keys.

Key Injection Facility (KIF): a secure service facility that injects encryption keys (e.g., symmetric or asymmetric keys) into a device, typically a POI Device. The injected encryption key is used, in particular embodiments, to encrypt data (e.g., consumer data, such as PAN data) received by the POI Device.

Merchant: an entity that provides or sells goods and/or services to consumers and, in various embodiments, purchases, orders, and/or employs one or more POI Devices and utilizes the P2PE Manager.

P2PE Manager: in various embodiments, an application for managing various state changes of a POI Device, for reporting state changes of a POI Device (or POI Devices), determining decryption key index names, and/or for providing reports for Merchants for compliance or other purposes.

P2PE Payload, Transaction Payload, or Payload: a bundle of information transmitted from a POI Device. A payload may include any variety of suitable information. As a non-limiting example, in particular embodiments, a payload includes consumer information, such as a card's PAN as well as a POI Device serial number. In various embodiments, a payload is sent to the P2PE Manager. In at least one embodiment, a payload is transmitted to a Payment Processor/Payment Network before decryption.

Payment Card Industry (PCI): generally, the debit, credit, prepaid, e-purse, e-wallet, ATM, and point of sale card industry and associated businesses.

Payment Processor/Payment Network: one or more entities (typically a third party) that processes payments (e.g., credit card transactions) for a Merchant.

PCI Security Council: a council originally formed by American Express, Discover Financial Services, JCB, MasterCard Worldwide, and Visa International for managing the PCI Data Security Standard. By meeting various PCI Security Council requirements, businesses can be deemed "PCI Compliant" or "PCI Validated."

PCI Validation/Validated (PCI Compliant): an entity may be deemed PCI Validated by meeting various criteria set forth by the PCI Security Council. PCI Validated companies and/or solutions may be listed by the PCI Security Council (e.g., on the PCI Security Council website or in other suitable locations).

Point of Interaction (POI) Device (Point of Entry Device): in various embodiments, a component of a point of sale system that enables a consumer to make a purchase at a Merchant, such as with a payment card. POI Devices may or may not be consumer-facing and may require a PIN number and/or other authentication. Non-limiting examples of POI Devices include magnetic card readers (e.g., for reading a payment card, such as a credit card) and near field communication (NFC) devices (e.g., for receiving a consumer's payment information from an electronic device, such as a mobile device). POI Devices may or may not be PCI Council approved devices.

Point to Point Encryption (P2PE): a combination of secure devices, applications, and processes that encrypt data from the point of interaction (for example, at the point of swipe) until the data reaches the solution provider's secure decryption environment.

Primary Account Number (PAN): an account number typically found on the front side of a payment card (e.g., a credit card number).

State(s): a recordable state and/or status of a particular device such as a POI Device. Various states and/or statuses may include "new," "active," "lost," "stolen," "tampered," "damaged," "malfunction," "quarantined," "in repair," "retired," and "destroyed."

State Changes: a recordable change in the state of a device, such as a POI Device. In a particular example, a POI Device state may be changed from "active" to "lost" based on various factors.

Overview

The present systems and methods relate generally to management of encryption processes, management of encryption devices, validation handling of encryption devices (including point-to-point encryption devices), and managing, assigning, and reporting state changes of encryption devices. According to particular embodiments, the present systems and methods track handling of decryption devices and their respective payloads (e.g., outputs of swipe data, etc.). It should be understood from the disclosure herein that the management of the encryption processes described herein may be, in some embodiments, PCI validated and compliant.

According to particular embodiments, the systems and methods herein are directed to secure encryption device handling. Particularly, the systems and methods herein are directed to: 1) receiving an indication of a state of a particular device; 2) receiving a payload from the particular device, including a device serial number and encrypted payload; 3) creating a record (e.g., a fingerprint) of the format of the payload and storing the record in memory; 4) receiving a second payload from the particular device, the second payload including the device serial number and a second encrypted payload; 5) retrieving the record of the format of the payload associated with the particular device from memory; 6) comparing the record of format of the payload to the format of the second payload; and 7) upon determining that that the format of the second payload does not match the record of the record of format of the payload, changing the state of the particular device to a tampered state.

In one or more aspects, the systems and methods herein are directed to facilitating decryption of encryption device payloads based on a device serial number included in the payload. In these aspects (and others), the system is configured to retrieve various information regarding the particular device from a database based on the device serial number. Such data may include, for example, a record of the format of a first payload of the particular device (as discussed above), a key index number indicating a base key used as the basis for encrypting a payload of the particular device, a state of the particular device, etc.

According to various aspects, the systems and methods herein are further directed to create a "fingerprint" of a particular device. Particularly, the system may be configured to create a fingerprint of the particular device to be used as a comparison to payloads received from the particular device to determine whether the particular device is compromised (e.g., the device has been stolen, hacked, etc.). The system may be configured to create the fingerprint of the particular device in any suitable way such as, for example, by parsing a first payload received from the particular device, determining the format of each segment of the first payload, recording the format of each segment of the first payload in an order of the payload.

In some aspects, the systems and methods herein are directed to creating reports regarding states and locations of encryption devices tracked by the system. In these aspects, the system is configured to receive a report request from a merchant, compile the report based on state information associated with encryption devices associated with the merchant, request that the merchant attest to the information included in the report, and provide the report to the merchant.

As will be understood by one of ordinary skill in the art, the systems and methods herein may be used by any suitable entity. Further, the systems and methods described herein may be utilized for any suitable encryption/decryption process, including, but not limited to, point-to-point encryption, encryption/decryption of medical data, encryption/decryption of social security numbers, etc. The following exemplary functionality of the systems and methods herein is included for the purpose of furthering understanding of the included systems and methods and is intended to be exemplary and non-limiting.

Exemplary P2PE Manager and Payments Functionality

Turing now to the figures, FIGS. 1A and 1B depict a high-level exemplary P2PE manager and payments environment and process. In general, FIGS. 1A and 1B show an exemplary path of an exemplary point of interaction (POI) device from a manufacturer (e.g., manufacturer 102) to a merchant (e.g., merchant 132) and the various processes and state changes associated with the exemplary POI device. FIGS. 1A and 1B further depict data received by the P2PE system 160, exemplary high level of data processing that occurs at the P2PE system, and an exemplary payment cycle.

FIG. 1A shows an exemplary P2PE manager and process wherein swipe (as will be understood by one of ordinary skill in the art, data may also be keyed into a user interface) data is sent from a merchant swipe terminal (e.g., a POI device) directly to a P2PE Payment System. FIG. 1B shows an exemplary P2PE manager and process similar to the process depicted in FIG. 1A, except swipe data is sent from a merchant swipe terminal to a payment network, then to the P2PE Payment System. These various exemplary features and differences will be further discussed below.

FIG. 1A depicts a manufacturer 102 of point of interaction (POI) devices (e.g., POI device 104). According to particular embodiments, manufacturer 102 produces POI device 104 in response to receiving a purchase order from a merchant or from a P2PE system (e.g., P2PE system 160). In various embodiments, manufacturer 102 produces POI device 104 (and any other POI devices) in any suitable way, as will be understood by one of ordinary skill in the art. In particular embodiments, manufacturer 102 produces POI devices designed to output a device serial number and information in a particular format, as will be further discussed herein.

POI device 104 may be any device suitable of receiving information from a consumer. In various embodiments, POI device 104 receives payment information, as discussed throughout this document, although it should be understood by one of ordinary skill in the art that POI device 104 should not be considered limited to only payment information.

POI device 104 may include any suitable components for receiving payment information (e.g., credit card magnetic strip information, payment information received from a mobile device, such as a smartphone, tablet, PDA, etc., chip information (e.g., from cards with embedded chips), payment information received from a check-out station, other sensitive information, such as medical records received from an electronic medical records system, etc.). In various embodiments, POI device 104 reads and/or receives payment information via a magnetic card reader for reading a card's magnetic strip (e.g., a credit card). In one or more embodiments, POI device 104 includes a pin-pad, biometric scanner (e.g., finger print or retina scanner), and/or chip reader for receiving secondary consumer identity-verification information. In at least one embodiment, POI device 104 is configured for receiving payment information via one or more radios, such as a near-field communications radio, a suitable wireless network connection radio, such as a Bluetooth, Bluetooth Low Energy (BLE), and/or Wi-Fi radio (e.g., POI device may receive payment information from an application (mobile wallet) included on mobile device via a "tap").

As will be further discussed herein, POI device 104 transmits information received from a consumer (e.g., payment information, biometric information, PIN information, etc.) to another system/device for processing. In various embodiments, POI device 104 is configured to encrypt received information upon receipt of said information. According to particular embodiments, POI device 104 transmits information received from the consumer with device information, such as a serial number associated with POI device 104 for identification of the POI device. In some embodiments, POI device 104 is configured to transmit the information received from the consumer and device information in a particular format, which may be used by a P2PE system (e.g., P2PE system 160) to form a "fingerprint" (e.g., an identifier based on the format and/or device information of POI device 104) for identifying transactions sent from POI device 104.

As will be understood by one of ordinary skill in the art, POI device 104 may be any POI device approved by the PCI Security Standards Council ("PCI SSC") or other suitable device for receiving information to be encrypted. Examples of PCI SSC-approved devices can be found on PCI SSC's website at https://www.pcisecuritystandards.org/approved-_companies_providers/approved_pin_transaction_security.php. In one or more embodiments, POI device 104 is a stand-alone swipe terminal, such as ID TECH's SecuRED™ SRED device. In some embodiments, POI device 104 is an all in one type mobile business solution, such as 4P Mobile Data Processing's FDA600-POS device. In at least one embodiment, the POI device 104 is a countertop terminal, such as Atos Worldline's Yomani device.

Still referring to FIGS. 1A/1B, manufacturer 102 ships POI device 104 via secure shipping 106 to a key injection facility (KIF) 110. As will be understood by one of ordinary skill in the art, secure shipping 106 may represent any suitable type of secure shipping known in the art, including, but not limited to, via FedEx, UPS, etc. and/or by shipping via air, ground, rail, etc.

Once received by KIF 110, in one or more embodiments, information regarding POI device 104 is entered into P2PE manager 166. In various embodiments, the information regarding POI device 104 includes a device serial number (e.g., to be matched later to swipe transactions). In at least one embodiment, the information regarding POI device 104 includes a firmware version number. In further embodiments, the information regarding POI device 104 includes a date of manufacture, the name of the manufacturer (e.g., manufacturer 102), etc.

Information regarding POI device 104 may be entered into the P2PE manager 166 in any suitable way, such as, for example, by user interface 180 or via an API interface. In various embodiments, a KIF employee scans in a serial number associated with POI device 104 via a suitable scanning mechanism (e.g., a hand-held barcode scanner or the like). In some embodiments, a KIF employee keys in a serial number associated with POI device 104 via a keyboard (or other suitable key-entry device, such as a touch screen). As will be understood by one of ordinary skill in the art, POI device 104 may be processed via any suitable security protocol and information about POI device 104 may be entered into any suitable system, such as a separate KIF inventory management system.

As shown in FIGS. 1A/1B, P2PE manager 166 may be operatively connected to user interface 180. User interface 180 may represent any number of user interfaces configured to interact with P2PE manager 166 and user interface 180 may be connected to P2PE manager 166 in any suitable way, such as via the Internet, LAN, WAN, Wi-Fi, etc. For example, user interface 180 may represent a user interface at KIF 110 used to input information regarding POI device 104 (as discussed above). Continuing with this example, user interface 180 may also represent a user interface at merchant 132 used to entered information regarding POI device 104 (e.g., when POI device 104 is received, to update the state of POI device 104, etc.). User interface 180, in this example, may represent a user interface at a third-party "Partner" (e.g., a hospital using an electronic medical records system or other entity wishing to encrypt and decrypt data). User interface 180 may be used to manually change the state of POI device 104 (e.g., from "Stored" to "Deployed") or view the state of POI device 104, as shown at 182. In some embodiments, user interface 180, via P2PE manager 166, may be configured to produce one or more reports 184 (as will be further discussed herein).

According to particular embodiments, once POI device 104 information is entered into P2PE manager 166, it is assigned a "state." The state of POI device 104 as indicated in P2PE manager 166 may be used to help ensure secure handling and chain of custody of POI device 104. For example, when first entered into the P2PE manager 166, POI device 104 is assigned a state of "New" in the P2PE manager 166. Once a key has been injected into POI device 104, the state may be changed to "Injected." Once received by a merchant (e.g., merchant 132), but not deployed/in use, POI device 104 may have a state of "Stored." Alternately, POI device 104 may be assigned a state of "DOA" (dead on arrival) if the device is damaged or non-functional. For example, P2PE manager 166 may be configured to discard, prohibit and/or block data (e.g., card swipe data), from a POI device that is listed in a "Tampered," "Dirty," or "Flagged" state to protect the system and/or the card swipe data.

Continuing with FIGS. 1A/1B, POI device 104 is stored at KIF 110 in a secured inventory room. The inventory room may be secured in any suitable way, such as, but not limited to, dual access, by lock and key, or by any suitable security protocol.

According to particular embodiments, upon order from a merchant, POI device 104 is injected with one or more base derivation keys ("BDKs") and is securely bagged, tagged, and packed for secure shipment to the merchant (e.g., merchant 132). According to at least one embodiment, a hardware security module ("HSM") array produces encryption/decryption keys for encrypting data received by the POI device 104. As will be understood by one of ordinary skill in the art, an HSM array may be located at a KIF or at a remote location. In the embodiment shown in FIGS. 1A/1B, KIF 110 and HSM array 162 are remote.

HSM array 162, shown in FIGS. 1A/1B as part of P2PE system 160, in various embodiments, creates a base derivation key (BDK), which is split into two parts, BDK 164A and BDK 164B for security purposes. BDK 164A and 164B are sent to KIF 110 (via two separate secure pathways) where they are received by two key part holders. BDK 164A and 164B may be sent to KIF 110 in any suitable manner, such as, for example, by courier, by mail, by fax, by email (encrypted or otherwise), etc. In particular embodiments, the two key part holders verify receipt of BDK 164A and BDK 164B via signature upon delivery, delivery receipt, etc.

In particular embodiments, the process continues with key assembly at step 114. The key assembly process is briefly described immediately below. However, it will be understood by one of ordinary skill in the art that this key assembly process is intended to be exemplary and any suitable key assembly process may be used. The first key part holder (e.g., the person with BDK 164A) enters the secured inventory room storing POI device 104 and enters BDK 164A into a tamper resistant security module ("TRSM"). The first key part holder leaves the secured inventory room. The second key part holder (e.g., the person with BDK 164B) enters the secured inventory room (e.g., after the first key part holder has exited the secured inventory room) and enters BDK 164B into the TRSM. According to particular embodiments, a third party separately validates the entries of the first key part holder and the second key part holder (e.g., via a key serial number (KSN) and check digit). Upon authentication of the key parts, the TRSM produces a cryptogram representing the (assembled) BDK 164 and transfers the cryptogram to a smart card. POI device 104 (and each POI device) is injected with a unique Initial Key derived from the BDK (e.g., from the smart card). As discussed herein, once POI device 104 is injected with the encryption key, its state in the P2PE manager 166 may be changed to "Injected."

Still referring to FIGS. 1A/1B, at step 116, POI device 104 is placed in a tamper evident bag and the bag is sealed with a tamper evident, serialized sticker. POI device 104 (in the tamper evident bag and sealed with the serialized sticker) is then, at step 118, sealed in a box (e.g., any suitable shipping container) for shipment to merchant 132 and given a tracking number. According to particular embodiments, the serial number on the serialized sticker and the tracking number for the shipment of POI device 104 is entered into P2PE manager 166 and associated with the record for POI device 104 in P2PE manager 166 for later verification by merchant 132 upon receipt of POI device 104. In various embodiments, once a tracking number is entered into P2PE manager 166, the state associated with POI device 104 may be changed.

At step 120, POI device 104 is securely shipped to merchant 132. POI device 104 may be securely shipped to merchant 132 in any suitable way, including by FedEx, UPS, USPS, etc. by air, ground, rail, etc.

Merchant 132 receives POI device 104 and registers receipt of POI device 104 with P2PE manager 166 as shown at step 134. In various embodiments, upon receipt of POI device 104, merchant 132 confirms that the tamper evident bag (see above) and the serialized sticker used to pack POI device 104 have not been tampered with. In particular embodiments, merchant 132 enters the serial number of POI device 104 (as printed on the outside of the shipping box or in some other location) and the serial number of the serialized sticker into P2PE manager 166. In one or more embodiments, the state associated with POI device 104 is changed to "Stored" in P2PE manager 166. Merchant 132 stores POI device 104 (in the tamper evident bag) until deployment.

At step 138, merchant 132 removes POI device 104 from the tamper evident bag for deployment. In various embodiments, merchant 132 changes the state of POI device 104 to "Deployed" in P2PE manager 166. It will be understood that, in various embodiments, P2PE manager 166 substantially automatically changes the state of POI Device 104 to "Deployed" based on receiving information (e.g., that the POI device 104 has been removed from the tamper evident bag).

At step 140, POI device 104 is deployed (e.g., connected a cash register, etc.) to accept payment card information. As further discussed herein, POI device 104 may be configured to accept any payment (or other) information, but for the purposes of simplicity and brevity, payment card information in the form of magnetic card swipe data will be discussed in regards to FIGS. 1A/1B.

Upon receiving magnetic card swipe data (e.g., a first or initial card swipe), in various embodiments, POI device 104 substantially automatically encrypts the magnetic card swipe data based on the encryption key injected into POI device 104 at step 114 above. In various embodiments, POI device 104 is configured to encrypt the swipe data immediately after receiving the swipe data. In particular embodiments, POI device 104 may receive swipe data in any suitable way, including, via magnetic read heads (if a credit/debit card with a magstripe is swiped), via a chip and pin reader, via near-field communications, etc.

In FIG. 1A, according to particular embodiments, upon receiving and encrypting swipe data, POI device 104 is configured to transmit the swipe data and other information (collectively, a "payload") to P2PE manager 166 for verification and decryption of the swipe data. According to particular embodiments, POI device 104's payload includes, in addition to the swipe data, a serial number associated with POI device 104 (e.g., the serial number assigned to POI device 104 by manufacturer 102 and recorded in P2PE manager 166 at KIF 110). In some embodiments, POI device 104's payload includes other information including PIN information, biometric information (e.g., POI device includes or is connected to one or more biometric readers, such as a finger print scanner), chip information, etc.

An alternate pathway for POI device 166's payload is shown in FIG. 1B, to be discussed herein. It will be understood by one of ordinary skill in the art that a POI device payload path as shown in FIGS. 1A and 1B is merely exemplary and a POI device payload may be routed through one or more entities and/or via pathways not shown in FIG. 1A or 1B.

At step 142, in response to receiving its first card swipe, POI device 104 transmits its first payload to P2PE manager 166 via internet 164. In particular embodiments, upon receipt of the first payload from POI device 104, P2PE manager 166 is configured to parse the first payload of POI device 104 and extract the serial number of POI device 104. In some embodiments, P2PE manager 166 then compares the extracted serial number of POI device 104 to a table of POI device serial numbers to determine whether POI device 104 is included in the table. In other words, in certain embodiments, P2PE manager 166 is configured to determine whether POI device 104 is a recognized device based on its serial number that is sent to P2PE manager 166 with each transaction payload.

Upon determining that POI device 104's serial number is included in P2PE manager 166, P2PE manager 166 may be configured to check the state associated with POI device 104. If, for example, POI device 104 has a state of "Deployed" in P2PE manager 166, upon successfully receiving the first swipe transaction, P2PE manager 166 may change the state of POI device 104 to "Active." An "Active" state in P2PE manager 166 generally denotes a state of securely receiving decrypted swipe transactions.

If, as another example, POI device 104 has a state of "Tampered" or "Stolen" or "Lost" in P2PE manager 166, P2PE manager 166 may be configured to discard the received payload and/or report the receipt of a payload from a POI device that is not listed as "Active" or "Deployed" to merchant 132 or any other suitable party and not process the encrypted swipe data (e.g., included in the payload). It should be understood based on discussions herein that the system can help detect fraudulent transactions based at least in part on the various states of P2PE manager 166. An exemplary list of state changes is shown at 182 in FIGS. 1A/1B and will be further discussed herein.

Continuing with the example shown in FIGS. 1A/1B wherein P2PE manager 166 has received a first payload from POI device 104, P2PE manager 166 creates a "fingerprint" to be associated (in memory) with POI device 104 at step 170. According to particular embodiments, the fingerprint for POI device 104 is created by parsing the payload sent by POI device 104 and recording the format, order, and number of data items included in the payload (e.g., opposed to the contents of the payload) and/or any firmware versions of software running on POI device 104. Exemplary fingerprint creation processes will be further discussed herein (e.g., at FIG. 4A). In various embodiments, the fingerprint is stored and used in future transactions to verify that data received from POI device 104 is secure (e.g., that POI device 104 has not been tampered with and/or is not malfunctioning).

According the embodiment shown in FIGS. 1A/1B, after the fingerprint analysis 170, P2PE manager 166 transmits the first payload from POI device 104 to HSM 162 for decrypting (e.g., using BDK 164). Once the payload is decrypted, the swipe data is re-encrypted to an encryption that can be decrypted by other entities in the payment process. Once the payload is re-encrypted, it is transmitted to a payment network 190 where the swipe data (e.g., credit card information)

is processed and sent on to an issuing bank 192 (money is debited from the consumer's account associated with the swiped card), acquiring bank 194, and finally to a depository bank 144 where money is deposited to the merchant (e.g., merchant's bank account).

In particular embodiments, the system operates essentially in the same way each time a payload is received from POI device 104 while the state associated with POI device 104 is "Active" (e.g., POI device 104 regularly receives swipe transactions). For example, a customer of merchant 132 swipes their credit card at POI device 104. POI device 104 transmits its payload, including POI device 104 serial number and encrypted swipe data to P2PE manager 166. Continuing with this example, P2PE manager 166 determines the serial number of the received payload (e.g., POI device 104's serial number) and looks up corresponding fingerprint information associated with POI device 104's serial number to verify that POI device 104 has not been tampered with at step 170. Once POI device 104's fingerprint has been verified, in this example, HSM 162 decrypts POI device 104's payload and then re-encrypts the swipe data and sends it on to the payment network 190, issuing bank, 192, acquiring bank 194, and depository bank 144 to complete the payment process.

Continuing with FIGS. 1A/1B, if POI device 104 is tampered with (e.g., in an attempt to steal consumer data), P2PE manager 166 is configured to block fraudulent transactions by not passing payloads to HSM 162 for decryption as shown in step 174. There are a number of ways that P2PE manager 166 may determine that POI device 104 has been tampered with and refuse to pass the payload on to HSM 162 for decryption. In a particular embodiment, P2PE manager 166 may receive a payload from POI device 104 that does not match the fingerprint associated with POI device 104 (e.g., the format of the payload has changed, the version number of the firmware used by the device has changed, etc.). In various embodiments, P2PE manager 166 may determine that a payload from POI device 104 has been tampered with by receiving a payload from POI device 104 after merchant 132 has recorded that POI device 104's state is "In Repair," "Damaged," "Retired," "Destroyed," or "Stolen" (e.g., P2PE manager should not be receiving a payload from POI device 104 and thus will not decrypt the payload). In many cases, if P2PE manager 166 determines that POI device 104 has been tampered with, then it will transmit a notification to merchant 132 and/or any other appropriate party, change the state of POI device 104 in the POI database 168 to "Tampered" and will no longer decrypt payloads from POI device 104.

FIG. 1B shows a process similar to that described above. In FIG. 1B, payloads from POI device 104 are first transmitted to payment networks 190 (but not decrypted) and then transmitted to P2PE system 160 (e.g., opposed to payloads being sent directly from merchant system 130 to P2PE system 160 as shown in FIG. 1A). Payloads are then processed, in various embodiments, as described above at the P2PE system 160 and sent back to payment network 190, then to issuing bank 192, etc. to complete the payment process.

System Architecture

FIGS. 2A and 2B are block diagrams depicting exemplary system architectures of the exemplary P2PE system of FIGS. 1A and 1B, respectively. These architectural components are organized into overarching processes for secure handling of devices and payloads (e.g., for decryption): secure device handling process 300, merchant data processes 400A and 400B, and payment system processes 500A and 500B. These major components are intended to be exemplary only and are used to assist in explaining the systems and methods herein. As will be understood, the following architectural components may be operatively connected in any suitable way and may include suitable processors, databases, firewalls, and the like. Further, the various components discussed herein may be distributed and operatively connected in any suitable way. For example, in various embodiments, the architectural components discussed below may be physically connected and located in the same room and/or may be connected via the Internet or private network and may be located remotely.

Secure POI Handling System

Secure POI handling system 300 is more fully described in this document in connection with FIG. 3. Secure POI handling system 300, according to particular embodiments, includes a point of interaction manufacturer 302 (e.g., manufacturer 102 in FIGS. 1A/1B) that produces and ships a POI device 350 via secure handling procedures to a key injection facility (KIF) 502. KIF 502 injects the POI device 350 with an encryption key and securely ships POI device 350 to a merchant. POI device 350 is included in merchant data processes 400A and 400B as further described herein.

POI manufacturer 302 manufactures devices that may be used with the systems and methods discussed herein. POI manufacturer 302 may manufacture any suitable device, including any POI device approved by the PCI Security Standards Council ("PCI SSC") or other suitable device for receiving information to be encrypted. Examples of PCI SSC-approved devices can currently be found on PCI SSC's website at https://www.pcisecuritystandards.org/approved_companies_providers/approved_pin_transaction_security.php. In one or more embodiments, POI device 350 is a stand-alone swipe terminal, such as ID TECH's SecuRED™ SRED device. In some embodiments, POI device 350 is an all in one type mobile business solution, such as 4P Mobile Data Processing's FDA600-POS device. In at least one embodiment, the POI device 350 is a countertop terminal, such as Atos Worldline's Yomani device.

As will be understood from discussions herein, POI manufacturer 302 is merely an exemplary manufacturer. In various embodiments, the system may be configured to decrypt any type of encrypted information (e.g., in a "decryption as a service" environment) from any suitable device. In these embodiments (and others), the manufacturer may produce any suitable encryption device for encrypting social security numbers, driver license numbers, personal data, patient information, etc., and thus, may not necessarily produce POI devices. However, for the purposes of clarity of and brevity, a POI manufacturer and POI devices are shown in the figures.

It will be understood by one of ordinary skill in the art that merchants and key injection personnel do not typically program POI devices (other than encryption key injection at a key injection facility). Thus, in many of the embodiments discussed herein, POI manufacturer 302 loads and/or programs POI device 350. In various embodiments, POI manufacturer 302 configures POI device 350 with particular firmware and/or a particular version of firmware. In further embodiments, POI manufacturer 302 configures POI device 350 with various hardware and software security features (e.g., software for encrypting swipe data substantially immediately after being read by POI device 350, hardware that destroys/erases any keys stored by POI device 350 upon tampering, etc.).

In particular embodiments, POI manufacturer 302 configures POI device 350 to transmit a payload of information, where the payload includes a specific set of information. In these (and other) embodiments, the payload may include any suitable information such as device serial number and/or any other unique device identifier, unique identifier and version number of the firmware installed on the device, date of device manufacture, device brand identifier, device model identifier, etc. In further related embodiments, the POI manufacturer 302 configures POI device 350 to transmit the payload in a particular format (e.g., portions of data in a particular order, numbers in a particular format such as hexadecimal, character, etc.). These configurations may be used by P2PE management system 510 (or 166) to identify particular POI devices (e.g., POI device 350 and/or POI device 104 (FIGS. 1A/1B) and to verify the authenticity of the received data via a fingerprint, as will be further discusses in relation to FIGS. 5A and 5B.

Although not shown in FIGS. 2A and 2B, POI manufacturer 302 may include computing devices operatively connected to P2PE management system 510 via any suitable connection.

KIF 502 includes any suitable computers, machines, etc. to receive encryption keys 562, send and receive data 512, securely inject POI device 350 with an encryption key, bag POI device 350 with a serialized tamper-resistant bag, and ship POI device 350 to a merchant. As discussed herein, in various embodiments, upon receipt of POI device 350, a user enters (e.g., keys, scans, etc.) information associated with POI device 350 into P2PE manager 166 (serial number, firmware version number, etc.). In these embodiments, the user may enter the information associated with POI device 350 via a bar code scanner operatively connected to a computing device, via a keyboard operatively connected to a computing device, via a touchscreen interface operatively connected to a computing device, etc.

Computing devices located at the KIF may be any suitable computing devices, including desktop computers, laptop computers, servers, tablets, other mobile devices, etc. In various embodiments, at least some of the computing devices located at the KIF are configured to connect to the P2PE management system 510 via a suitable user interface. In some embodiments, information is exchanged between computing devices located at the KIF and the P2PE management system 510 via email, http, or other suitable protocol.

According to particular embodiments, KIF 502 includes a tamper resistant security module ("TRSM") for assembling key parts (as discussed above, in various embodiments, the base derivation key is sent to the KIF in two parts and is reassembled). The TRSM may be any suitable TRSM incorporating physical protections, including, for example, tamper-evident seals, hardened casings, and hardware and software to erase the contents of the TRSM upon detection of tampering. In various embodiments, upon combining and validation of key parts, the TRSM produces a cryptogram representing the base derivation key. In some embodiments, the cryptogram is transferred to a smart card.

The smartcard may be any suitable smartcard. In various embodiments, the smartcard is a smartcard with a chip including one or more processors for key generation, signature, and/or encryption. In particular embodiments, the smartcard is equipped with software for creating suitable algorithms, such as hashing algorithms. In at least one embodiment, the smartcard is operative for communicating with the TRSM and suitable key injection devices (e.g., Key Loading Devices, (KLDs)). The smartcard may include other features, such as tamper-resistant measures, tamper notification measures, anti-tearing measures, etc.

According to particular embodiments, the smart card is not used. In these embodiments (and others), the base derivation key is sent to the KIF in two parts and is reassembled as a KLD, without the use of the smartcard.

In various embodiments, the KIF 502 includes one or more KLDs for injecting POI devices with encryption keys. KLDs may be any suitable key loading/key fill devices and, in various embodiments, are secure cryptographic devices (SCDs).

According to various embodiments, once injected with an encryption key, POI device 350 is packaged in a tamper evident bag and shipped to the merchant for deployment.

Merchant Data System

As shown in the embodiments depicted in FIG. 2A/2B, merchant data system 400 includes POI device 350 deployed to receive payment transactions and POI device 350 operatively connected to a payment transaction processor 416A/416B. In FIG. 2A, payment transaction processor 416A is shown as part of the payment system processes 500 (e.g., the payment system provides the payment system transaction processor 416A to the merchant). FIG. 2B shows third party transaction processor 416B as excluded from payment system processes 500 (e.g., third party transaction processor 416B is provided by a party other than the payment system, such as by the merchant or by a suitable partner). An exemplary merchant data process 400A and an exemplary merchant P2PE report process 400B are more fully described in this document in connection with FIGS. 4A and 4B, respectively. The merchant may include any suitable computing devices, point of sale devices, servers, databases, processors, etc.

As will be understood by one of ordinary skill in the art, POI device 350 may be operatively connected to any suitable merchant point of sale system. In various embodiments, POI device 350 is operatively connected to a cash register, which may be digital, analog, touchscreen, etc. According to particular embodiments, POI device 350 is operatively connected to a mobile device, such as a mobile phone, tablet, etc running software to accept payment information. In further embodiments, POI device 350 is operatively connected to a desktop computing device for completing sales.

In the embodiments shown in FIGS. 2A/2B, POI device 350 is operatively connected to payment transaction processor 416A/416B. It will be understood by one of ordinary skill in the art that POI device 350 may be directly connected to payment transaction processor 416A/416B or may be indirectly connected to payment transaction processor 416A/416B (e.g., POI device 350's payloads are transmitted through other components of a point of sale system to payment transaction processor 416A/416B). In various embodiments, third party transaction processor 416A/416B may represent any suitable number of servers, processors, etc. and may be located in any suitable location, including at the merchant or at a location remote from the merchant.

As shown in FIG. 2A, third party transaction processor 416A is operatively connected (via Internet 209) to P2PE management system 510. According to this embodiment (and other embodiments), third party transaction processor 416A is configured to transmit one or more payloads from POI device 350 to P2PE management system 510 for processing. In particular embodiments, third party transaction processor 416A is configured to receive payments from issuer 214 (e.g., payments purchase made via POI device 350).

Alternately, as shown in FIG. 2B, third party transaction processor 416B is operatively connected (via Internet 209 or a private network (PN)) to one or more card networks 202, P2PE management system 510, and issuer 214. In this embodiment (and others), POI device 350 payloads are transmitted to third party transaction processor 416B, then, via Internet 209, to the payment system processes 500 for decryption and re-encryption, then the re-encrypted payment data is transmitted by Internet 209 and/or by PN to card networks 202.

The merchant system may include any number of suitable computing devices (not shown in FIGS. 2A/2B). These merchant computing devices may be any suitable computing devices, such as desktop computers, laptop, computers, tablets, etc. and may be operatively connected to the P2PE management system 510. The merchant computing devices, in various embodiments, enable users at the merchant to input information regarding POI device 350 to be transmitted to P2PE management system 510 (e.g., state change information, tracking information, etc.). In one or more embodiments, the merchant computing devices may also be configured to produce various auditing reports regarding P2PE compliance.

Payment System

In the embodiment shown in FIGS. 2A/2B, payment system 500 includes KIF 502, P2PE management system 510, and hardware security module (HSM) 560. In FIG. 2A, payment system 500 also includes payment system transaction processor 416A (as discussed above).

P2PE management system 510 may include any suitable software and/or hardware components, including servers, mobile computing devices, desktop computers, one or more databases, and any number of suitable processors. According to particular embodiments, P2PE management system 510 is configured to manage states of various POI devices (e.g., POI device 350). In these embodiments (and others), P2PE management system 510 may utilize any number of suitable tables and databases to store tables of information regarding the various states of POI devices. In particular embodiments, P2PE management system 510 includes one or more processors for receiving state changes from computing devices, receiving information regarding state changes of various POI devices, determining whether the state of a particular POI device should be changed based on received information, etc.

According to various embodiments, P2PE management system 510 includes one or more databases and one or more processors for receiving identification data associated with various POI devices (e.g., POI device 350), such as a device serial number, a device (encryption) key serial number, key sequence number, a device version number, a device firmware number/indicator, etc. In one or more embodiments, P2PE management system 510 is configured to store the received identification information and, in at least one embodiment, indexing the identification and other information associated with a particular POI device by the device serial number. For example, in a particular embodiment, P2PE management system 510 receives a payload of information from a merchant including a particular device serial number. Continuing with this example, P2PE management system 510 is configured for parsing the payload to extract the particular device serial number and for searching and locating additional device information based on the particular device serial number.

As a second particular example, P2PE management system 510 receives a payload of information from a third-party payment processor (e.g., the payment payload is sent from a merchant POI device to the third-party payment processor then to the P2PE management system). However, in this second particular example, the third-party payment processor sends a portion of the payload, which has already been parsed. Continuing with the second particular example, the P2PE management system 510 receives a third-party payment processor identifier, a key sequence number, and any encrypted payment information to be decrypted.

In various embodiments, P2PE management system 510 includes at least one database and at least one processor for creating and storing identifiers associated with POI devices (and/or any suitable encryption device or system). In some embodiments, P2PE management system 510 is configured to create a device identifier or "fingerprint" based on the format of one or more payloads received from a particular POI device (e.g., POI device 350). In these embodiments (and others), P2PE management system 510 is configured to compare the format of future payload received from the particular POI device to the fingerprint to verify the authenticity of the payload (e.g., that the payload has not been tampered with and/or compromised in some way.).

According to one or more embodiments, P2PE management system 510 includes various processors and databases for creating audit reports for merchants. In these embodiments (and other embodiments), P2PE management system 510 is configured to receive a request for an audit report from a computing device associated with a merchant and access one or more tables configured to store information associated with various POI devices associated with the merchant. P2PE management system 510, in these embodiments, is further configured to aggregate, summarize, and facilitate the display (e.g., display on a screen of a computing device at the merchant, send to a printer of a computing device at the merchant, etc.) of the information associated with the various POI devices associated with the merchant.

As will be understood by one of ordinary skill in the art, any of the above mentioned processors may perform more than one function described and any of the above mentioned databases may store more than one type of information. Thus, the discussion above should not necessarily limit the various processors disclosed herein as having only the functionality discussed above.

In various embodiments, P2PE management system 510 is operatively connected to HSM 560, which may represent any number of HSMs, including an array of HSMs. In various embodiments, HSM 560 includes suitable one or more processors and one or more databases for creating and storing encryption keys. In particular embodiments, HSM 560 includes at least one processor and at least one database for receiving payloads, for deriving encryption keys from payload information, for decrypting payment data included in such payloads, re-encrypting at least a portion of a payload, including the payment information, and transmitting the re-encrypted portion of the payload to a card network (e.g., card network 202) via the Internet 209 and/or a private network (PN).

According to particular embodiments HSM 560 is a device that provides FIPS 104-2 Level 3 certified physical and logical protection to cryptographic keys or other suitable PCI-compliant HSM. An example of such an HSM is the SafeNet Luna EFT HSM. Other examples of PCI approved HSMs can be found at https://www.pcisecuritystandards.org/approved_companies_providers/approved_pin_transaction_security.php.

Exemplary System Processes
Exemplary POI Handling Process (FIG. 3)

FIG. 3 depicts a high-level flow chart of an exemplary secure device handling process 300 as shown in FIGS. 2A/2B. In various embodiments, this POI handling process may help verify a secure chain of custody for a POI device. To briefly summarize, in a particular embodiment, as a POI device is transported from and handled by different entities, the POI Manager assign various states to the POI device. In these particular embodiments (and others), the POI Manager verifies that the POI device has been assigned the correct sequence of states before facilitating the decryption of a payload of the POI device. This secure POI handling process, in particular embodiments, helps identify whether POI devices have been tampered with and/or switched (e.g., with a nefarious POI device) during the transport of a POI device between the time of manufacture to the time of deployment at a merchant. POI handling process 300, as shown in FIG. 3 and described immediately below may help illustrate at least one embodiment of this POI handling process.

Beginning at step 330, the system is configured to receive particular POI device identification information at the P2PE management system 510. In various embodiments, the particular POI device identification information includes a serial number associated with the particular POI device (e.g., POI device 350 in FIGS. 2A/2B). In particular embodiments, the particular POI device identification information includes version of the firmware installed on the particular POI device. In further embodiments, the particular POI device identification information includes any other suitable information, such as model, device type, device manufacture date, etc.

The system may be configured to receive the particular POI device identification information from any suitable entity in any suitable way. In particular embodiments, the particular POI device identification information is transmitted (e.g., via encrypted electronic packets) from a computing device at a key injection facility (KIF). In some embodiments, the particular POI device identification information is received from a computing device associated with the manufacturer. In further embodiments, the particular POI device identification information is input by a person into a computing device operatively connected to the POI Manager.

At step 332, the system is configured to, in response to receiving the particular information associated with POI device 350, set the state of POI device 350 to indicate that the POI device is new/ready for programming. (e.g., the system is configured to set the state of the particular POI device to "New"). In various embodiments the system is configured to change the state of the POI device to New by adding the POI device (or associated identifier) to a table or list of POI devices with a New status. In further embodiments, the system is configured to change the state of the POI device by including the state of the POI device in a table with a POI device identifier (e.g., the POI device is listed by identifier on a table and the state associated with the POI device changes). In still further embodiments, the information associated with the POI device in the system may include various bits that indicate a state (e.g., information about POI devices include bits indicating each state and can be set to on or off to indicate the state of the device). In this embodiments (and others), the system may be configured to change the bit associated with the New state to on or to "1".

At step 334, the system is configured to receive an indication that the particular POI device is injected with an encryption key. As discussed herein, in various embodiments, POI devices are stored at a KIF until they are injected. In some embodiments, once the particular POI device is ordered from a merchant (or at any other suitable time), the particular POI device is injected with an encryption key under special security protocol (as discussed elsewhere herein).

The system may be configured to receive the indication that the particular POI device is injected with the encryption key in any suitable way. According to particular embodiments, once injected, a user at the KIF logs into the P2PE Manager (via a suitable computing device) and indicates that the particular POI device has been injected. In some embodiments, the system may be configured to receive the indication that the particular POI device is injected automatically from a computing device linked to the key injection equipment and/or certain protocol devices associated with injecting the particular POI device.

At step 336, based at least in part on receiving the indication that the particular POI device is injected with the encryption key, the system is configured to change the state of the particular POI device to indicate that the POI device has been injected (e.g., assign an "Injected" state). In particular embodiments, the system is configured to receive the indication that the particular POI device is injected by a user manually changing the status of the particular POI device from New to "Injected." The system may be configured to change the state of the POI device in any suitable way, including (but not limited to) the ways discussed in relation to changing the particular POI device state to "New" at step 332.

At step 338, the system is configured to receive information regarding shipping the particular POI device. In various embodiments, the particular POI device is packed for shipment from the KIF to a merchant. In these embodiments (and others), the system is configured to receive various information regarding the shipping of the particular POI device such as a tamper-resistant bag number (e.g., serial number), a box number, a tracking number, merchant number, address/shipping destination, and/or any other suitable information for tracking and/or verifying the shipment of the particular POI device.

At step 340, the system is configured to receive data from a merchant indicating receipt of the particular POI device. In various embodiments, the system is configured to receive the data from the merchant indicating receipt of the particular POI device by receiving the serial number of the particular POI device. In particular embodiments, the system is configured to receive the data from the merchant indicating receipt of the particular POI device by receiving the tracking number and/or tamper resistant bag serial number associated with the POI device. In some embodiments, the system may be configured to receive the data indicating the receipt of the particular POI device in any other suitable way.

At step 342, based on receiving the data from the merchant, the system is configured to determine whether the particular POI device has been compromised during shipment. In various embodiments, the system is configured to determine whether the particular POI device has been compromised during shipment by comparing the data received from the merchant (e.g., at step 340) to the information regarding shipping the particular POI device (e.g., at step 338). According to particular embodiments, the system is configured to look up the device based on the device serial number and verify that the tracking information, tamper resistant bag serial number, etc. match. In these embodiments, the system verifies these numbers/identifiers to ensure that the particular POI device has been shipped from the KIF to the merchant without tampering or without someone swapping out the particular POI device (e.g., for a POI device that is programmed to send cardholder information to another location or any other nefarious task).

The system may be configured to compare the data received from the merchant to the information regarding shipping the particular POI device in any suitable way. In various embodiments, the system is configured to store the information regarding the shipping the particular POI device in a table associated with the particular POI device's serial number (e.g., a serial number created by the manufacturer and input to the system at the KIF). In these embodiments, upon receipt of the serial number and data from the merchant indicating receipt of the particular POI device (e.g., the information at step 340), the system is configured to look up the information regarding shipping the particular POI device by looking up the particular POI device's serial number and accessing a table with the appropriate header (e.g., "KIF shipping information" or the like) to find the information regarding shipping the particular POI device.

At step 344, the system is configured to change the state of the particular POI device to indicate that the particular POI device has been received by the merchant (but not deployed). In various embodiments, the system is configured to change the state of the POI device to "Stored" to indicate that the particular POI device is stored at the merchant.

The system may be configured to change the state of the particular POI device in any suitable way. In various embodiments, the system is configured to change the state of the particular POI device by receiving an indication to change the state of the particular POI device from a computing device associated with the merchant (e.g., a user selects or inputs a notification to change the state of the particular POI device). According to particular embodiments, the system is configured to automatically change the state of the particular POI device upon determining that the particular POI device has not been compromised during shipment (e.g., at step 342). In further embodiments, the system may be configured to At step 346, the system is configured to receive an indication that the particular POI device is deployed. In various embodiments, the system may receive an indication from a computing device (e.g., a manual indication from a user) that the particular POI device is deployed (e.g., ready to receive swipe transactions). In one or more embodiments, the system is configured to receive an indication that the particular POI device is deployed by receiving an indication at a user-interface that the particular POI device is ready for deployment, and in response, the system changes the state of the particular POI device to indicated deployment (e.g., changes the state of the POI device from "Stored" to "Deployed").

It should be understood by one of ordinary skill in the art and from the discussions herein that the state of the particular POI device may change and/or vary from the sequence discussed above. In a particular example, the merchant could receive the particular POI device and determine that it is damaged. Continuing with this particular example, the merchant could then indicate to the system that the particular POI device is damaged and the system could change the state of the particular POI device to indicate that the POI device is damaged (e.g., a "Damaged" state). As discussed below, once in the Deployed state, the particular POI device (e.g., POI device 350) is ready to receive swipe data, as described below in reference to FIG. 4A.

Exemplary Merchant Data Process (FIG. 4A)

Referring to FIG. 3, above, once a particular POI device (e.g., POI device 350), is received by a merchant and deployed, the particular POI device is, in various embodiments, ready to receive customer transactions. As will be understood by one of ordinary skill in the art, the particular POI device may require additional set-up by the merchant, such as, for example, connection to a payment processing computing device, additional software set-up, etc.

Turning to FIG. 4, at step 430, the particular POI device receives customer data. As discussed herein, the particular POI device may receive payment transaction data (card swipe data, etc.) and other customer verification information, such as, for example, biometric data (finger print, retinal scan, etc.) chip and pin data, PIN data, etc.

At step 432, immediately upon receiving the customer data, the particular POI device is configured to encrypt the customer data. In various embodiments, the particular POI device may be configured to encrypt the customer data based on the encryption key(s) that have been injected. In some embodiments, the particular POI device is configured to encrypt the customer data via an internal encryption scheme. In further embodiments, the particular POI device is configured to encrypt the customer data via an encryption key that is sent to particular POI device with each transaction.

At step 434, the particular POI device is configured to compile a payload to be transmitted to a payment processor. In various embodiments, the payload includes the encrypted customer data. In one or more embodiments, the payload includes the device serial number. In at least one embodiment, the payload includes the device serial number and/or firmware number. In further embodiments, the payload includes a manufacture date of the particular POI device. In still further embodiments, the payload includes various other information such as an encrypted PIN or other verification information associated with a customer and/or other information to identify the transaction (e.g., date of transaction, merchant, cashier number, etc.).

The particular POI device may be configured to compile the payload in any suitable format, which may be used by the system to create a fingerprint for the particular POI device as discussed herein. In various embodiments, the particular POI device is configured to compile the payload in a string of data representing various data items of the payload. In these embodiments (and others), various components of the payload string may be formatted in character, XML, or hexadecimal format.

The payload may include any suitable components. In various embodiments, the payload includes an indication of the format of the components (e.g., hexadecimal, XML, etc.). In particular embodiments, the payload includes an indication of the particular encryption (cypher) algorithm, such as, for example, RAW (e.g., data is unencrypted), triple data encryption standard ("TDES") indicating that the DES derived unique key per transaction ("DUKPT") encryption scheme has been used to encrypt the payload data, advanced encryption standard indicating that the AES DUKPT encryption scheme has been used to encrypt the payload data.

In various embodiments, the P2PE Manager includes an indication of a particular type of encryption associated with a particular device based on the particular device's serial number. In these embodiments, and others, the system is configured to transmit an indication of the particular type of encryption to the HSM based on the particular devices serial number.

According to particular embodiments, the payload includes card swipe data. The card swipe data may include any or all of the various tracks of data encoded in a card's magnetic stripe. As will be understood by one of ordinary skill in the art, in various embodiments, a card's magnetic stripe contains three distinct tracks of encoded data, each read by a magnetic card reader. In these embodiments, the system may be configured to encrypt and compile each track of card data. In some embodiments, each track of card data may include different information. In further embodiments, each track of card data may include at least some of the same information.

The particular POI device may be configured to compile each track of card data in any suitable way. In various embodiments, the particular POI device is configured to compile each track of card swipe data as card track format with each track formatted as a clear set of data (e.g., no encryption), followed by an encrypted set of data (e.g., the card swipe data for the particular track), followed by a dummy set of encrypted data (e.g., encrypted random data that does not represent the card swipe data). In particular embodiments, each of the clear, encrypted, and dummy sets of data may be in a character or hexadecimal format.

The particular POI device may output the above described data, for example, in the following format:

FORMAT_CIPHERED_[TRACK1][_TRACK2]
[_TRACK3]

The particular POI device may be configured to include additional data in the payload. According to particular embodiments, the particular POI device is configured to include a key serial number ("KSN") and/or device serial number ("DSN") in the payload (e.g., a key serial number indicating how the HSM should decrypt the various encrypted tracks and a device serial number as discussed herein to identify the particular POI device). In these embodiments (and others) the KSN and DSN may be formatted in either character or hexadecimal format. In further embodiments, the particular POI device is configured to include a hardware version number and/or a firmware version number, each of which may be formatted in character or hexadecimal format (or may be empty). As will be understood by one of ordinary skill in the art, the above components of the payload may be formatted in any suitable format and may arranged in the payload in any suitable way. For example, the TRACK1 data above may come before or after the FORMAT and/or CIPHERED data. Likewise, the track data may be in any other order (e.g., TRACK3 data may come before TRACK1 data). Further, the KSN or DSN data may be located anywhere in the payload string.

In a particular example, the payload string may be formatted as:

FORMAT_CIPHERED_[TRACK1][_TRACK2]
[_TRACK3][_KSN][_DSN][_HWV_HARDWARE]
[_FMV_FIRMWARE]

As will be further discussed below, in particular embodiments, the system uses this payload string and the format of each data component to create a unique fingerprint for each device.

At step 436, the particular POI device is configured to transmit the payload to a payment processing system. According to particular embodiments, the particular POI device is configured to transmit the payload to a third party for payment processing. In at least one embodiment, the system is configured to transmit the payload to a payment processing system associated with the P2PE Management System 510. In some embodiments, the system is configured to transmit the payload to any suitable intermediary for processing before being sent to the payment processor. For the sake of brevity, this section of this document refers to a payment processing system, which may mean any of the above.

The particular POI device may be configured to transmit the payload to the payment processing system in any suitable way. According to some embodiments, the particular POI device is configured to transmit the payload to the payment processing system via the internet. In one or more embodiments, the particular POI device is configured to transmit the payload to the payment processing system via a secure private network. In some embodiments, the particular POI device is configured to transmit the payload to the payment processing system via a LAN, WAN, Wi-Fi, hardline, or other suitable connection.

As will be understood from discussions herein, the particular POI device, in various embodiments is a "dumb" device. Thus, the particular POI device, in these embodiments (and others) is configured to receive data (whatever the data may be), encrypt the data based on the firmware installed, compile and transmit the payload without regard to where the data is headed, whether the POI device has been tamper with, whether the POI device has been stolen, etc. It should also be understood that the particular POI device may have a variety of other security measures installed, such as, for example, tamper resistant casing, a circuit designed to self-destruct upon tampering, various audio or visual alarms, etc.

Exemplary P2PE Report Process (FIG. 4B)

Referring to FIG. 4A above, once a particular POI device (e.g., POI device 350), is received by a merchant and deployed, the particular POI device is, in various embodiments, ready to receive customer transactions. In these embodiments (and others), the merchant may be required to produce one or more audit reports and attest to the state of the POI device (and any other POI devices in the merchant's possession). According to particular embodiments, the systems and methods herein are configured to gather information and product such audit reports.

Turning to FIG. 4B, the system, at step 431, is configured to receive a request for an audit report from a computing device associated with a merchant. In various embodiments, the system is configured to receive the request for the audit report from the computing device associated with the merchant by receiving log in information (e.g., which may identify the particular merchant) associated with a particular user (e.g., username, password, and/or other suitable credentials) and receiving an indication that the particular user would like an audit report. In one or more embodiments, the system is configured to receive the request from the audit report from the computing device associated with the merchant by receiving the audit request from a particular computing device that is dedicated to communicating with the system (e.g., a computing terminal that is configured to only function with the P2PE Management System).

The audit report may be any suitable audit report that includes any suitable information. In various embodiments, as discussed above, the audit report may include information associated with one or more devices associated with the merchant and/or the status of each of the one or more devices associated with the merchant. According to particular embodiments, the audit report includes an attestation of the information associated with each of the one or more devices associated with the merchant. In further embodiments, the audit report includes an attestation by the user (e.g., representing the merchant) that the user has read, and/or that the merchant is in compliance with, a compliance manual (e.g., a P2PE Instruction Manual or the like).

At step 433, the system is configured to, in response to receiving the request for the audit report, retrieve merchant device information associated with the merchant. As discussed herein, in various embodiments, the system is configured to receive information regarding the chain of custody of various devices. In these embodiments (and others), the system is configured to locate and retrieve information regarding each device associated with the merchant. Such merchant device information may include any suitable information, including, but not limited to: a device identifier, a device location, a device serial number, number of transactions processed by a device, a device status (e.g., "active", "lost", "tampered", "stored", etc.), etc.

According to particular embodiments, the audit report (e.g., requested at step 431) may include an attestation to that the user (e.g., representing the merchant) has read, and/or that the merchant is in compliance with, a compliance manual. In these embodiments (and others), the system is configured to retrieve a copy of the compliance manual to display to the user.

At step 435, the system is configured to display the merchant device information. In various embodiments, the system is configured to display the merchant device information including the merchant device identifier, merchant device location, and merchant device status. In particular embodiments, the system is configured to display the copy of the compliance manual.

At step 437, the system is configured to request attestation of the merchant device information. In particular embodiments, the system is configured to request attestation by the user clicking one or more check boxes. In various embodiments, the system is configured to request attestation by the user typing or electronically signing their name. In further embodiments, the system is configured to request attestation by the user entering in a code, filling out a document, clicking a button, scrolling to the end of a page or electronic document, etc.

At step 439, the system is configured to receive an indication of attestation (e.g, the system is configured to receive an indication that the user has checked a box, filled out a form, signed an electronic form, etc.). At step 441, the system is configured to, in response to receiving the indication of attestation, compile the audit report, the audit report including the identifier of each device associated with the merchant, the status of each merchant device, and the indication of attestation. The system may be configured to compile the audit report in any suitable way and the audit report may be in any suitable format.

At step 443, the system is configured to transmit the audit report to the computing device associated with the merchant. The system may be configured to transmit the audit report to the computer device associated with the merchant by displaying the audit report, accessing and causing the computing device associated with the merchant to print the audit report, etc. In various embodiments, the system is configured to transmit a copy of the attested to audit report to various other entities, such as auditing entities, etc.

Exemplary Payment System Processes (FIG. 5A & FIG. 5B)

FIGS. 5A and 5B are exemplary processes performed by the P2PE Management System (e.g., P2PE Management System 510). FIG. 5A is an exemplary payload integrity verification process and FIG. 5B is an exemplary fingerprint creation process, which may be used as part of the payload integrity verification process.

Exemplary Payload Integrity Verification Process

Turning to FIG. 5A, the system, at step 530, is configured to receive a payload originating from a device, the payload including encrypted information and a device serial number. In various embodiments, the system is configured to receive the payload from a payment point of interaction device (e.g., a credit card swipe device). In particular embodiments, the system is configured to receive the payload from a health records computing device (e.g., a device that transmits sensitive health records for storage by the system). In further embodiments, the system is configured to receive the payload from a computing device associated with financial information (e.g., bank account information, etc.). In still further embodiments, the system is configured to receive the payload from any other suitable device, such as a device transmitting sensitive information such a driver's license number, a social security number, etc.

The payload may include any suitable information (e.g., any suitable string of particular elements). In various embodiments, the payload includes encrypted information and the device serial number. In particular embodiments, the payload includes a key serial number that is used to decrypt the encrypted information. In one or more embodiments, the payload includes a device firmware number. In further embodiments, the payload includes any other suitable device or payload information associated with the device, transaction, and/or merchant in custody of the device.

The encrypted information may be any suitable information that has been encrypted, such as, for example, a social security number, a credit card number, payment information, a driver's license number, medical record information, a birthdate, a bank account number, a routing number, a name, etc. As discussed herein, the payload may be in any suitable format, which may be used as a fingerprint for device identification.

At step 532, the system is configured to parse the payload to extract the device serial number. In various embodiments, the system is configured to parse the payload to extract the device serial number by separating the encrypted information from the unencrypted information and determining which one or more unencrypted numbers are included in the device serial number. In particular embodiments, the payload includes a string of numbers and information and the device serial number is located in a particular location of the string (e.g., the device serial number may be the first number, the second number, the fifth number, etc.). As will be understood by one of ordinary skill in the art, the method of parsing the payload my depend upon the structure/format of the payload.

At step 534, the system is configured to retrieve a serial number table from the database, the serial number table comprising one or more serial numbers. At step 536, the system is configured to compare the device serial number to the serial number table to determine whether the device serial number is included in the serial number table. The system may be configured to compare the device serial number to the serial number table in any suitable way including searching for the device serial number, comparing the device serial number to all serial numbers in the table, and/or by using some other indicator (first number, etc.) to narrow down the one or more serial numbers included in the serial number table that may match the device serial number. It should be understood by one of ordinary skill in the art that the serial number table may be more than one suitable serial number table.

At step 538, the system is configured to, upon determining that the device serial number is included in the table, retrieve, from memory, a fingerprint associated with the device, wherein the fingerprint is an identifier for the device based on the format of one or more payloads that originated from the device (see FIG. 5B regarding discussion of fingerprint creation). In particular embodiments, the system is configured to create the fingerprint associated with the device, as further discussed herein. In further embodiments, the system is configured to receive the fingerprint associated with the device from third party system (e.g., a third-party system creates the fingerprint and transmits the fingerprint to the system. In still further embodiments, the device fingerprint is manually entered by one or more users.

At step 540, the system is configured to compare the payload to the fingerprint to determine whether the device has been compromised. In various embodiments, the system is configured to compare the format of the payload (e.g., the order of the particular elements of the payload) to the fingerprint (e.g., a representation of the format of a first payload receive from the device) to verify the format matches the fingerprint. In some embodiments, the system is configured to compare various elements of the payload to the format, such as the key serial number, the device firmware number, etc. to the fingerprint to determine whether the device has been compromised (e.g., the if the compared element does not match the corresponding portion of the fingerprint, the device may have been compromised).

At step 542, the system is configured to, upon determining that the device has not been compromised, facilitating decryption of the encrypted information. In various embodiments, the system is configured to facilitate decryption of the encrypted information by transmitting the encrypted information (and/or the entire payload) to an HSM for decryption. Upon determining that the device has been compromised, the may be configured to discard the payload, (e.g., not facilitate decryption of the encrypted information), notify the merchant, change a status of the device (e.g., as discussed herein), and/or no longer accept payloads from the device.

Exemplary Payload Fingerprint Process

Generally, FIG. 5B shows an exemplary process for generating a device fingerprint. Beginning with FIG. 5B, the system, at step 531, is configured to receive a payload from a device. The system may be configured to receive the payload from any suitable device, such as, for example, any suitable device discussed above regarding step 530.

At step 533, the system is configured to determine whether the received payload is the first payload received from the device. In various embodiments, the system is configured to determine whether the received payload is the first payload received from the device by comparing a serial number included in the received payload to a list of serial numbers of devices from which payloads have been received. In one or more embodiments, the system is configured to determine whether the received payload is the first payload received from the device by comparing a device identifier received from a user-interface (e.g., a user inputs device serial numbers) to an identifier included in the device payload.

At step 535, the system is configured to, based on determining that the received payload is the first payload received from the device, parse the received payload. The system may be configured to parse the device payload in any suitable way as discussed herein. At step 537, the system is configured to determine the format of the payload. The system may be configured to determine the format of the payload in any suitable way. Further, the format of the payload may vary and may be in any suitable form as discussed herein, such as CHR, HEX, Base64, or any other suitable format. In particular embodiments, the system may only store the format of the payload but may not store track data.

For example, the payload format may be in the following format:

FORMAT_CIPHERED_[TRACK1][_TRACK2]
[_KSN][_DSN]

Continuing with the above example, "CIPHERED" is the encryption algorithm and may be, for example, RAW (data is unencrypted), TDES (DES DUKPT), or AES (AES DUKPT). Further, in this example, each TRACK is formatted at 1, 2, or 3, "+" and a CHR string "+" a string a numbers in HEX format, "+" a string of numbers in HEX format. Thus, in this example, TRACK1 above is formatted as 1+CHR+HEX+HEX. In this example, the fingerprint may be FORMAT is in HEX format, CIPHERED is TDES, TRACK1 is in 1+CHR+HEX+HEX format, TRACK2 is in 2+CHR+HEX+HEX format, KSN (key serial number) is in HEX format, and DSN (device serial number) is in HEX format. Therefore, the system may be configured to create a fingerprint, in this example of:

HEX_TDES_1+CHR+HEX+HEX_2+CHR+HEX+
HEX_HEX_HEX

At step 539, the system is configured to store in memory a fingerprint for the device, the fingerprint based on the format of the received payload. At step 541, the system is configured to compare each subsequent payload received from the device to device fingerprint (e.g., to determine whether the device has been compromised). In various embodiments, the system is configured to determine that the device has been compromised when the format of a particular subsequent payload does not match the device fingerprint (e.g., someone has changed something about the output of the device, such as the device firmware version number, etc.).

Exemplary UML Diagrams

FIGS. 6-14 show UML diagrams illustrating various sequences of the present systems and methods. Particularly, FIGS. 6-14 depict exemplary processes for point-to-point encryption (P2PE) transactions, wherein payloads may include encrypted data, unencrypted data, or both. It will be understood by one of ordinary skill in the art that these exemplary processes may be used in any type of transaction, including, but not limited to end to end encryption transactions. The lifelines and major process components will be used throughout (e.g., QSAPI is represented by QSAPI 602 across FIGS. 6-14, wherever present).

In various embodiments, as shown in FIG. 6, a customer (e.g., merchant) posts data to be processed to a web application (e.g., via a web browser) at POST request 616. Based on the data included in the post, the web application chooses a script to run. Generally, FIGS. 6-14 depict two script lifelines, qsapi-process-3.8.php 602 and validator.class.php 1320, which are further described below. As shown in FIGS. 6-14, the system uses at least two databases, a POI database (FIGS. 9 and 12) and a Quickswipe database (FIGS. 6, 8, 9, 10, 12, and 14). In various embodiments, the POI database is a database that POI Manager uses for persisting information on various devices. According to one or more embodiments, the Quickswipe database is a database operatively connected to qsapi-process-3.8.php 602 and used to store various qsapi-process-3.8.php 602 information.

Exemplary Overall System Sequence

Turning to FIG. 6, the lifeline qsapi-process-3.8.php 602, in the embodiments shown, implements majority of the P2PE management system functionality via a Quickswipe API ("QSAPI 602"). It should be understood by one of ordinary skill in the art that QSAPI 602 functionality may be implemented by any suitable number of APIs, scripts, and/or functions. For simplicity and brevity, only QSAPI 602 will be discussed. According to particular embodiments, and shown in FIG. 6, QSAPI 602 starts with instantiating specialized .PHP classes that encapsulate different aspects of processing as described herein, including, but not limited to instances of Device, DevicesController and poi classes.

Continuing with FIG. 6, "Device" class 610 is a base class for all supported devices (e.g., POI devices, etc.). In particular embodiments, each type of device (e.g., each device brand, model, etc.) associated with the system has a corresponding child class inherited from the Device class 610 (e.g., each brand of POI device has a separate child class). In various embodiments, each child class includes one or more aspects of a device's output inherited from the class, including, but not limited to device payload format (e.g., XML or binary format), an indication of whether data is encrypted etc. According to particular embodiments, the Device class 610 receives information regarding each type of device via a fromString(device output) string, as shown in FIG. 6, to instantiate the appropriate Device child class instance. In various embodiments, the Device class 610 uses the information in the appropriate child class to parse device payload (see fetch(device output)) for data decryption, if a device payload includes encrypted data. In the embodiments shown in FIG. 6, the system uses Luna EFT HSM Device 608 to decrypt device payload data.

In various embodiments, Device class 610 selects a child class to be instantiated via a method fromString( ) (e.g., based on the device type, etc.), creates a new( ) instance, and calls a fetch( ) method. According to particular embodiments, the fetch method parses device payload and stores parsed data. For example, Device class 610 method fromString( ) returns a reference that contains the parsed data of a particular payload. Continuing with this particular example, the fromString reference may contain card track 1, 2, 3 data, a device serial number, and/or device firmware and hardware information (as discussed herein, the device payload data may include any suitable information).

Continuing with FIG. 6, DevicesController class 612 is a controller class that, in particular embodiments, encapsulates several activities that QSAPI 602 uses to determine whether a particular device has been compromised, tampered with, etc. In particular embodiments, a DevicesController class 612 instance is initialized with Quickswipe database 606 accessors. In various embodiments, DevicesController class 612 transmits an indication of any such indication of device tampering to the POI Manager (e.g., P2PE Management System, see FIG. 9), upon detection. According to one or more embodiments, DevicesController class 612 retrieves and stores data at Quickswipe database 606 table entitled device_use.

An instance of poi class 614 is initialized by class_construct( ) method. The construct method, according to particular embodiments, retrieves an HSM key index from the POI Manager (see FIG. 9) for legacy devices (e.g., one or more device payloads received by the system from one or more devices that are not P2PE certified). As shown in FIGS. 6-14, example poi processes are logIncident( ) and getHsmKey( ). Generally, in various embodiments, poi class 614 posts requests to POI Manager and interprets POI Manager responses (see FIG. 9).

As shown in FIG. 6, Luna EFT HSM Device 608 (e.g., HSM Device 608), in various embodiments, is specialized hardware to encrypt or decrypt data. As discussed herein, according to particular embodiments, a particular device is injected with a key at a Key Injection Facility. In these embodiments (and others), this base key is stored in an HSM Device (e.g., HSM Device 608) in an internal table. Continuing with this embodiment, in order to decrypt encrypted data from the particular device payload, a decrypt( )method passes a key index included in the particular device payload to the HSM Device 608 to derive the associated transaction key. In some embodiments, POI Manager stores HSM key indexes in POI database (as shown in FIG. 9) and QSAPI 602 retrieves various base keys by device serial number.

In various embodiments, once the Device class 610 inherited child class for a particular device is received, QSAPI 602 determines which one or more sub-processes (which "opt") to complete (e.g., sub-processes 620, 630, and 640). At step 620, if QSAPI 602 determines that the particular device payload does not contain a device serial number, QSAPI 602 processes the particular Device as non-P2PE device (e.g., accordingly, in these embodiments (and others), QSAPI 602 does not retrieve or request the POI Manager's access key from the Quickswipe database).

Continuing with step 630, if QSAPI 602 determines that the particular device payload includes a device serial number, QSAPI 602 compares the device payload with a fingerprint associated with the device (as discussed herein) at "Capture Device," which is further discussed at FIG. 8. In one or more embodiments, upon completion of the Capture Device process, QSAPI 602 receives a record of a device_use table in Quickswipe database 606.

At step 630, if QSAPI 602 determines that the particular device payload includes encrypted data, QSAPI 602 retrieves an HSM key index from POI Manager to pass to HSM Device 608 for decryption as further described in FIG. 11 (Get HSM Key Index). If the Get HSM Key Index process returns a non-positive value, QSAPI 602 will terminate with sending an error response. Otherwise Get HSM Key Index returns an HSM key index for use in decrypting any encrypted data included in the payload of the particular device. See FIG. 12 for details on the Update Key Index process.

According to particular embodiments, upon completion of the Update Key Index process (e.g., at FIG. 12), QSAPI 602 returns a decrypt(key index) method, which is passed to Device class 610. In various embodiments, Device class 610 uses the key index provided by the decrypt(key index) method to transmit necessary data to the HSM Device 608 for decrypting the encrypted data of the payload of the particular device. In one or more embodiments, Device class 610 transmits a DECIPHER2 Luna EFT command (including the key index and cipher data) to HSM Device 608, which decrypts the encrypted payload data of the particular device. In further embodiments, once decrypted, the decrypted payload data is transmitted from the HSM Device 608 to Device class 610 and decrypted clear tracks data are parsed by parseDecryptedData( ). In these embodiments (and others), relevant data, including, but not limited to, parsed card tracks, PAN data, an expiration date, a cvv number, card holder data, etc. are included in a data container CardData as shown in FIG. 6.

At step 640, in some embodiments, upon determining that the particular device payload does not contain encrypted data, QSAPI 602 calls Device class 608 method parseTracks( ) to get a data container (e.g., CardData container) filled with a parsed card number, an expiration date, card holder data, etc. At step 650, QSAPI 602 validates the data included in the CardData container, which is further discussed regarding FIG. 13. At step 660, QSAPI 602 processes any exceptions at a Handle Exceptions process, which is further discussed regarding FIG. 14.

Exemplary Capture Device Sequence

Turning to FIG. 8, the exemplary capture device process discussed herein is implemented in embodiments where the payload of the particular device includes the device serial number. QSAPI 602 calls Device class 608 for a string that identifies certain features of the payload of the particular device (e.g., a device fingerprint as discussed herein and exemplary process shown in FIG. 7), including, for example, device payload format (e.g., XML, hexadecimal string, etc.), an indication of whether a portion of the device payload is encrypted, number of tracks included, etc. After a device payload format is determined, in various embodiments, QSAPI 602 calls DevicesController class 612 method captureDevice( ) with a device serial number, a device fingerprint, and a flag that indicates whether a portion of the device payload is encrypted.

In one or more embodiments, DevicesController class 612 searches for a record of the particular device in a device_use record table at the Quickswipe database 606 using the device serial number of the particular device (e.g., at CaptureDevice( ) above). Upon finding a record of the particular device at the Quickswipe database 606, DevicesController class 612, in particular embodiments, examines various aspects of the device_use information (e.g., stored in the Quickswipe database 606). In some embodiments, DevicesController class 612 determines whether the system has marked the particular device as tampered (e.g., the system has changed the state of the particular device to tampered). In these embodiments, the system is configured to determine that the particular device has been marked as tampered if the date_disabled column returns a "NOT NULL" value (e.g., indicating that the particular device is marked as tampered by the POI Manager). Upon receiving a value of NOT NULL for date_disabled column, according to particular embodiments, the captureDevice( ) method returns a "FALSE" value to QSAPI 602. In further embodiments, upon receiving the "FALSE" value for the captureDevice( ) method, the QSAPI 602 sends an error response to a user and terminates execution of the process (e.g., does not proceed with decryption of any encrypted payload information received from the particular device).

In various embodiments, upon receiving a value other than NOT NULL for the date_disabled column, the system determines whether the encryption flag for the particular device matches an encryption indication stored at the Quickswipe database 606. In particular embodiments, the system compares the received encrypted flag (e.g., as received with the payload at captureDevice( ), above) against the encryption flag stored for the particular device at Quickswipe database 606. According to particular embodiments, QSAPI 602 considers a change of encrypted flag (output was encrypted, but now data is not encrypted) for a particular device as an indication that the particular device is compromised or tampered and should be disabled. In these embodiments, the captureDevice( )method returns FALSE to the QSAPI 602, which sends an error response to the user and terminates execution of the process. For more information regarding disabling devices, see FIG. 9.

According to one or more embodiments, upon determining that the received encryption flag matches the stored encryption indication at the Quickswipe database 606, the system is configured to compare the device payload format with a stored fingerprint for the particular device stored at the Quickswipe database 606. According to particular embodiments, QSAPI 602 considers a change in device fingerprint as a temporary failure (several intermittent factors can cause device payload format to be different, such as, for example, unreliable USB connection of device to the personal computer may cause a change in device payload format), for more details regarding temporary failure, see FIG. 10. In further embodiments, in response to the system determining that the particular device payload format does not match the fingerprint, captureDevice( ) returns FALSE, which results in QSAPI 602 sending an error response to the user and to terminating execution of the process.

If all above checks were evaluated to False, captureDevice( ) method returns a current value of DEVICE_USE row to QSAPI 602. Upon determining that the particular device ss used for the first time (device_use row NOT FOUND), DevicesController class 612 inserts a new device_use row with a passed encrypted flag and a device fingerprint in the Quickswipe database 606.

Exemplary Disable Device Sequence

Turning to FIG. 9, according to various embodiments, POI Manager 910 tracks the chain of custody of devices. According to various embodiments, POI Manager 910 is implemented as collection of .PHP classes responsible for several activities. In some embodiments, POI Manager 910 returns an appropriate controller class, such as the DevicesController class 612 based on the type of request posted by QSAPI 602. As shown in FIG. 9, POI Manager 910 receives an indication to disable decryption of a particular device (e.g., the particular device discussed in the embodiments above) because the payload of the particular device is unencrypted (e.g., but should have been decrypted). In the embodiment shown in FIG. 9, the particular device will be disabled in Quickswipe database 606 and disable date will be set to the value of current date and time. POI Manager 910 changes the state of the particular device to tampered in POI database 920.

Exemplary Increment Failed Count Sequence

Turning to FIG. 10, QSAPI 602, in various embodiments, tracks each failed encryption attempt for every device with a known serial number. According to particular embodiments, when a particular device's information is captured for the first time, the system adds a new row to device_use table with failed_count set to 0 and max_failed_count set to a hardcoded limit (5, 10, etc.). In one or more embodiments, each time a payload is received from the particular device, QSAPI 602 runs a validation check. In further embodiments, QSAPI 602 increments the failed_count value each time a validation check fails. In still further embodiments, if the failed_count reaches the max_failed_count hardcoded limit (e.g., 2, 5, 7, 10, 20, etc.), the system disables the particular device (e.g., and no longer decrypts payloads received from the particular device). In particular embodiments, the system may be configured to reset the failed_count value to 0 with each passed validation check. In some embodiments, the system may be configured to increment the failed_count value with each failed validation check, regardless of whether there has been an intermediate passed validation check. An exemplary disable device process is described above in regards to FIG. 9.

Exemplary Get HSM Key Index Sequence

Upon determining that a particular device payload includes encrypted data, QSAPI 602 follows the exemplary process shown in FIG. 11. As discussed herein, in various embodiments, the particular device payload includes an integer value indicating a number of times a decryption key value was derived from a base key. In some embodiments, HSM Device 608 derives the encryption key from its internal copy of the base key and uses the derived encryption key to decrypt encrypted data in the particular device payload.

According to particular embodiments, QSAPI 602 retrieves a poi_accessKey corresponding to the particular device from poi class 614. In one or more embodiments, upon determining that the $poi_{13}$ accessKey is NULL or empty, poi class 614 returns a legacy_key_index (e.g., indicating that the particular device is a "legacy device" and not part of a P2PE decryption scheme). In various embodiments, upon determining that the particular device serial number is not empty and poi_accessKey is not NULL, poi class 614 requests an hsm_key_id from POI Manager Web Server 1110, as shown in FIG. 11.

As will be understood by one of ordinary skill in the art, in some embodiments, the HSM Device 608 stores more than one base key in an internal HSM Device table. Thus, in these embodiments (and other embodiments), the HSM Device 608 requires an indication of which of the more than one base key to use to decrypt the particular device payload. As described above, in some embodiments, POI Manager stores HSM key indexes in POI database (as shown in FIG. 9) and QSAPI 602 retrieves various base keys by device serial number and transmits the HSM key index (which indicates the base key to use to decrypt the particular device payload) to the HSM Device 608.

Exemplary Update Key Index Sequence

FIG. 12 shows an exemplary update key index sequence. As shown in the embodiment in FIG. 12, if the system determines that the key index associated with a particular device has changed, then the system is configured to disable the particular device, as discussed above.

Exemplary Validation Sequence

Turning to FIG. 13, in the embodiment shown, upon receiving a payload from a particular device, QSAPI 602 determines whether the payload includes track1 data in a correct format, track2 data in a correct format, or both (e.g., by checking the fingerprint associated with the particular device and/or other appropriate record). If the payload does not include track1 data in the correct format, track2 data in the correct format, or both, QSAPI 602 sends an error response to a user and terminates execution of the process. Continuing with this sequence, if the system determines the payload includes track1 data in the correct format, track2 data in the correct format, or both (or any suitable number of tracks), in particular embodiments, QSAPI 602 proceeds validating track1, track2 or both. According to particular embodiments, card track data shall be non-empty string of numbers 0-9, which pass mod 10 check at validator.class.php 1320. In one or more embodiments, the system is configured to, upon successful validated card of the card track number, DevicesController class 612 resets device_use.failed_count (as discussed above) for the particular device to zero (0).

CONCLUSION

Aspects, features, and benefits of the claimed invention(s) will become apparent from the information disclosed in the exhibits and the other applications as incorporated by reference. Variations and modifications to the disclosed systems and methods may be effected without departing from the spirit and scope of the novel concepts of the disclosure.

It will, nevertheless, be understood that no limitation of the scope of the disclosure is intended by the information disclosed in the exhibits or the applications incorporated by reference; any alterations and further modifications of the described or illustrated embodiments, and any further applications of the principles of the disclosure as illustrated therein are contemplated as would normally occur to one skilled in the art to which the disclosure relates.

The foregoing description of the exemplary embodiments has been presented only for the purposes of illustration and description and is not intended to be exhaustive or to limit the inventions to the precise forms disclosed. Many modifications and variations are possible in light of the above teaching.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope. Accordingly, the scope of the present inventions is defined by the appended claims rather than the foregoing description and the exemplary embodiments described therein.

What is claimed is:

1. A computer system for creating a fingerprint for a device, the computer system comprising the device operatively connected to a device management system, the device management system comprising at least one processor operatively coupled to at least one database, the at least one processor configured for:
   receiving a first payload from the device, the first payload comprising data in a particular format, a device indicator comprising a unique identifier used for identifying the device, and an indication of a version of firmware running on the device;
   creating the fingerprint for the device, the fingerprint comprising a section format for each of one or more distinct sections of the particular format in a particular order and the indication of the version of the firmware running on the device;
   storing a record of the fingerprint for the device and the unique identifier at the at least one database;
   parsing the particular format of the first payload into the one or more distinct sections of the particular format;
   determining the section format of each of the one or more distinct sections;
   creating a record of the section format of each of the one or more distinct sections in the particular order; and
   comparing a format of each subsequent payload received from the device to the fingerprint for the device to determine whether the device has been compromised.

2. The computer system of claim 1, wherein the at least one processor is further configured for, upon determining that the device has been compromised, changing a state of the device to indicate the device is compromised.

3. The computer system of claim 2, wherein the at least one processor is further configured for only decrypting payloads of devices with states indicating they have not been compromised.

4. The computer system of claim 1, wherein comparing the format of each subsequent payload received from the device to the fingerprint for the device to determine whether the device has been compromised comprises:
   receiving a second payload from the device, the second payload comprising second data in a second particular format and a second device indicator, the second device indicator comprising a second unique identifier used for identifying the device;
   retrieving the fingerprint from the at least one database based on the second device indicator; and
   comparing the second particular format to the fingerprint to determine whether the device has been compromised.

5. The computer system of claim 4, wherein comparing the second particular format to the fingerprint to determine whether the device has been compromised comprises comparing the second format of each of one or more distinct sections of the second particular format to the section format for each of one or more distinct sections of the fingerprint.

6. The computer system of claim 5, wherein the at least one processor is further configured for, upon determining that the device has been compromised, transmitting a message to a user indicating that the device has been compromised.

7. The computer system of claim 6, wherein the at least one processor is further configured for, upon determining that the device has been compromised, disregarding the second payload without decrypting any data.

8. A computer system for creating a fingerprint for a device, the computer system comprising the device operatively connected to a device management system, the device management system comprising at least one processor operatively coupled to at least one database, the at least one processor configured for:
   receiving payloads from a particular device, each payload comprising encrypted and unencrypted data in a format;
   the first payload from a particular device comprising a device indicator comprising a unique identifier used for identifying the device and an indication of a version of firmware running on the device;
   creating the fingerprint for the device, the fingerprint comprising a section format for each of one or more distinct sections of the particular format in a particular order and the indication of the version of the firmware running on the device, creating the fingerprint for the device comprising:

parsing the particular format of the first payload into the one or more distinct sections of the particular format;

determining the section format of each of the one or more distinct sections; and creating a record of the section format of each of the one or more distinct sections in the particular order;

comparing the format of each payload from the particular device to the fingerprint associated with the particular device; and upon determining that the format of a particular payload of the payloads received from the particular device does not match the fingerprint associated with the particular device, declining to decrypt the encrypted data of the particular payload and transmitting a notification of declining to decrypt the encrypted data to a user computing system associated with a user.

9. The computer system of claim 8, wherein the at least one processor is further configured for, upon determining that the format of the particular payload of the payloads received from the particular device does not match the fingerprint associated with the particular device, changing a status associated with the particular device from active to tampered.

10. The computer system of claim 8, wherein each payload from the particular device includes one or more segments of data in a particular order.

11. The computer system of claim 10, wherein each of the one or more segments of data included in the payload from the particular device is in a particular format.

12. The computer system of claim 11, wherein the particular format for a particular segment of the one or more segments is a character format.

13. The computer system of claim 12, wherein the particular format for a second particular segment of the one or more segments is a hexadecimal format.

14. The computer system of claim 8, wherein the at least one processor is further configured for:

receiving payloads from a second particular device, each payload comprising encrypted and unencrypted data in a second format;

comparing the second format of each payload from the second particular device to a second fingerprint associated with the second particular device; and upon determining that the format of a second particular payload of the payloads received from the second particular device does not match the second fingerprint associated with the second particular device, declining to decrypt the encrypted data of the second particular payload and transmitting a notification of declining to decrypt the encrypted data to a second computing system associated with a second user.

15. The computer system of claim 14, wherein the fingerprint and the second fingerprint are not the same fingerprint.

16. A computer-implemented method for creating a fingerprint for a device, the method comprising:

providing a device capable of encrypting data;

providing a computer system operatively coupled to the device, the computer system comprising:

a decrypting means for decrypting data received from the device;

a fingerprint creation means for creating a fingerprint associated with the device;

at least one database; and at least one processor operatively coupled to the decrypting means, the fingerprint creation means, and the at least one database;

receiving, by the at least one processor, a first payload from the device, the first payload comprising data in a particular format, a device indicator comprising a unique identifier used for identifying the device, an indication of the version of the firmware running on the device, and encrypted data;

creating, by the fingerprint creation means, a fingerprint for the device, the fingerprint comprising a section format for each of one or more distinct sections of the particular format in a particular order and the indication of the version of the firmware running on the device;

creating the fingerprint for the device further comprising parsing the particular format of the first payload into the one or more distinct sections of the particular format, determining the section format of each of the one or more distinct sections, and creating a record of the section format of each of the one or more distinct sections in the particular order;

storing a record of the fingerprint for the device and the unique identifier at the at least one database and changing a state of the device to active by the at least one processor;

comparing, by the at least one processor, a second particular format of a subsequent payload received from the device to the fingerprint for the device to determine whether the device has been compromised; and upon determining that the device has not been compromised, decrypting, by the decrypting means, encrypted data of the subsequent payload.

17. The computer-implemented method of claim 16, the method further comprising the steps of:

receiving, by the at least one processor, the subsequent payload from the device, the subsequent payload comprising data in the second particular format and the device indicator; and retrieving, by the at least one processor, the fingerprint from the at least one database for comparing the second particular format to the fingerprint.

18. The computer-implemented method of claim 17, the method further comprising the steps of, upon determining that the device has been compromised, declining, by the at least one processor, to decrypt the encrypted data of the subsequent payload.

* * * * *